US011326168B2

(12) United States Patent
Hu et al.

(10) Patent No.: US 11,326,168 B2
(45) Date of Patent: May 10, 2022

(54) USE OF POTASSIUM CHANNEL INHIBITOR FOR TREATING DEPRESSION

(71) Applicant: ZHEJIANG UNIVERSITY, Zhejiang (CN)

(72) Inventors: Hailan Hu, Hangzhou (CN); Yihui Cui, Hangzhou (CN); Yan Yang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 16/679,197

(22) Filed: Nov. 9, 2019

(65) Prior Publication Data

US 2020/0149051 A1 May 14, 2020

Related U.S. Application Data

(63) Continuation of application No. PCT/CN2018/086021, filed on May 8, 2018.

(30) Foreign Application Priority Data

May 9, 2017 (CN) .......................... 201710322245.X

(51) Int. Cl.
| | | |
|---|---|---|
| *A61K 48/00* | (2006.01) | |
| *C07H 21/04* | (2006.01) | |
| *C12N 15/113* | (2010.01) | |
| *A61P 25/24* | (2006.01) | |
| *A61K 31/135* | (2006.01) | |
| *A61K 31/138* | (2006.01) | |
| *A61K 31/44* | (2006.01) | |
| *A61K 31/55* | (2006.01) | |
| *A61K 38/17* | (2006.01) | |

(52) U.S. Cl.
CPC ........ *C12N 15/1138* (2013.01); *A61K 31/135* (2013.01); *A61K 31/138* (2013.01); *A61K 31/44* (2013.01); *A61K 31/55* (2013.01); *A61K 38/177* (2013.01); *A61P 25/24* (2018.01); *C12N 15/113* (2013.01); *C12N 2310/14* (2013.01); *C12N 2310/531* (2013.01)

(58) Field of Classification Search
CPC ........................ C12N 15/113; C12N 2310/531
See application file for complete search history.

(56) References Cited

FOREIGN PATENT DOCUMENTS

CN 104338135 B 2/2015

OTHER PUBLICATIONS

Ohno et al. (Brain Research, 1178, 2007, 44-51).*
Brasko et al. (Brain Struct Funct, 2017, 222, 41-59 (published online Feb. 15, 2016)).*
Written Opinion of the International Search Authority in the International Application No. PCT/CN2018/086021, dated Nov. 12, 2018.
English Translation of Written Opinion of the International Search Authority in the International Application No. PCT/CN2018/086021, dated Nov. 12, 2018.
Fan Li, Role of Inwardly Recitifying Postassium Channel Kir4.1 in Oligodendrocyte Development and Myelin Formation. Biophysical Journal, Mar. 15, 2017, No. 03, E059-96, China Master's Theses Full-Text Database, China.
Kazuharu Furutani et al. The Structural Basis for Antidepressants Block Being Confined to Kir4.1. Biophysical Journal, vol. 96, issue 3, pp. 465a-465a.
First Office action of Chines Patent Application No. 201810432839.0, which claims priority to Chinese Patent Application No. CN201710322245.X, dated Aug. 31, 2020.
Hui Sun, Moduation Kv7 channel is a key regulator of dopaminergic neuronal excitability and depression-like behaviour. Biophysical Journal, Aug. 31, 2016, No. 02, E071-17, China Doctor's Theses Full-Text Database, China.
Supplementary European search report and Written Opinion of the EP 18798117.0, dated Jan. 27, 2021.
Andrews J M et al: "Contemporary management of depression", American Journal of Medicine, Excerpta Medica, Inc, United States, vol. 97, No. 6, Dec. 19, 1994 (Dec. 19, 1994), pp. S24-S32, XP023307550, ISSN: 0002-9343, DOI: 10.1016/0002-9343(94)90360-3.
Yukihiro Ohno et al. Inhibition of astroglial Kir4.1 channels by selective serotonin reuptake inhibitors. Brain Res. Oct. 31, 2007;1178:44-51.
Su Suwen et al. Inhibition of Astroglial Inwardly Rectifying Kir4.1 Channels by a Tricyclic Antidepressant, Nortriptyline. J Pharmacol Exp Ther. Feb. 2007;320(2):573-80.
Original and English Translation of Second Office action of Chines Patent Application No. 201810432839.0, which claims priority to Chinese Patent Application No. CN201710322245.X, dated Apr. 28, 2021.

* cited by examiner

*Primary Examiner* — Amy H Bowman
(74) *Attorney, Agent, or Firm* — Pattao, LLC; Junjie Feng

(57) ABSTRACT

In light of a discovery that astroglial Kir4.1 in lateral habenula drives neuronal bursts in depression, the present disclosure provides a pharmaceutical agent and a method of use thereof for treating depression. The pharmaceutical agent can inhibit an activity of an astroglial potassium channel, and especially suppress expression or functionality of Kir4.1, in astrocytes in the lateral habenula of a subject so that bursting activity of neurons in the lateral habenula of the subject can be suppressed. The pharmaceutical agent can include a vector expressing a target nucleotide sequence in the astrocytes in the lateral habenula, whose expression is configured to suppress Kir4.1 expression by RNA interference, or to block Kir4.1 functionality by a dominant negative effect of a mutant Kir4.1 protein. The pharmaceutical agent can alternatively comprise a small molecule compound, or an active macromolecule such as an anti-Kir4.1 antibody, configured to directly inhibit the astroglial potassium channel activity.

7 Claims, 21 Drawing Sheets

Specification includes a Sequence Listing.

Kir4.1 floxed mice

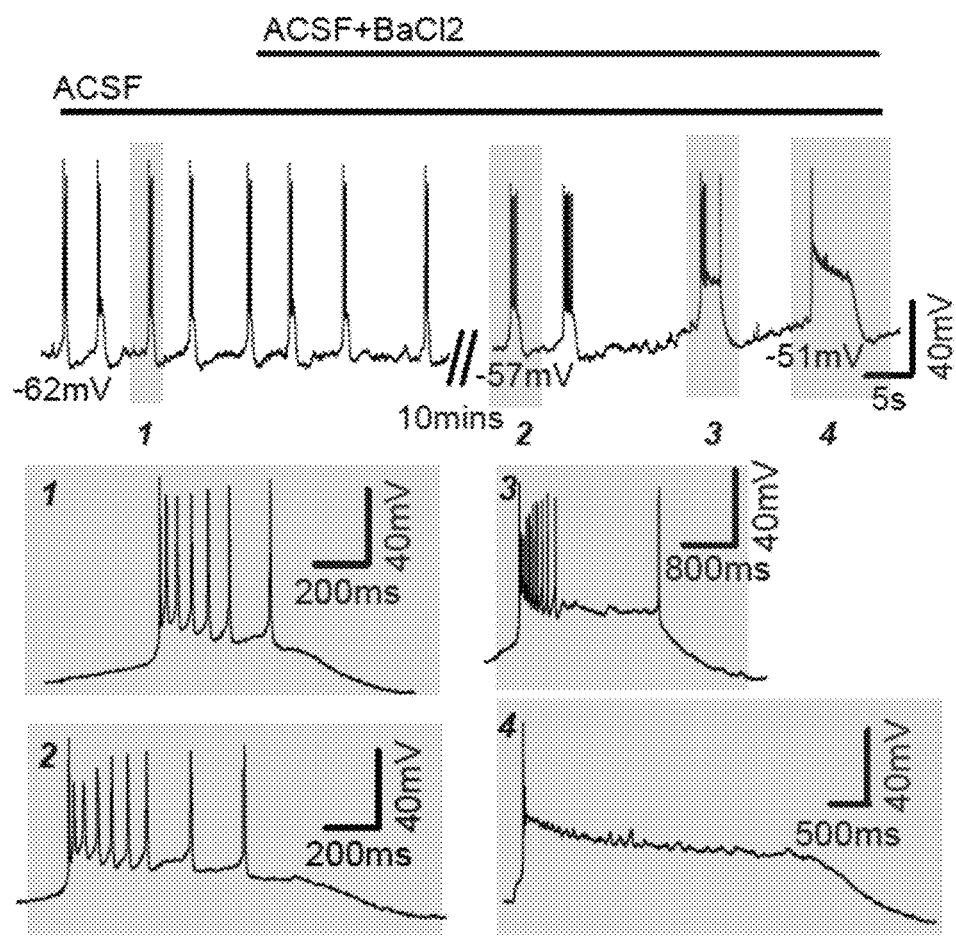
FIG. 4G
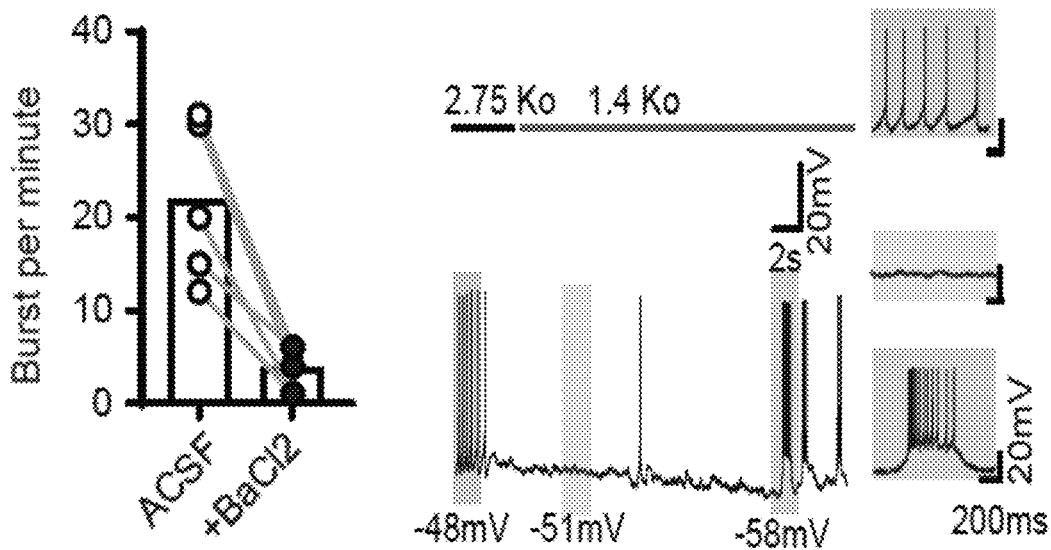
FIG. 4H
FIG. 4I

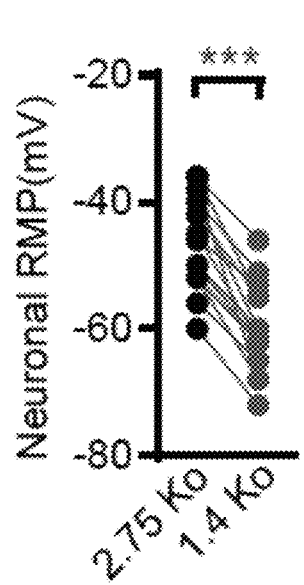 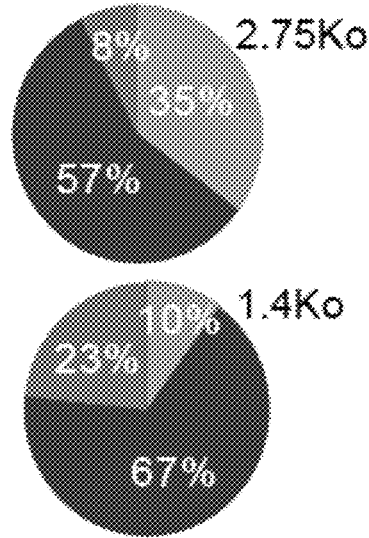
FIG. 4J          FIG. 4K
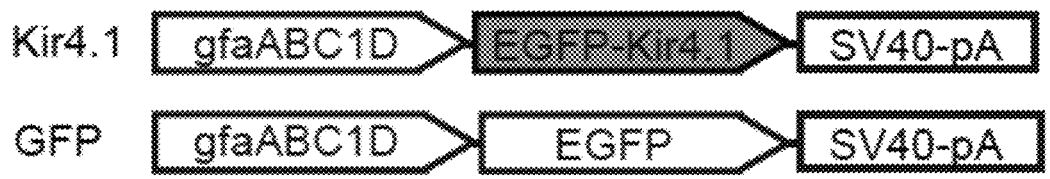
FIG. 5A
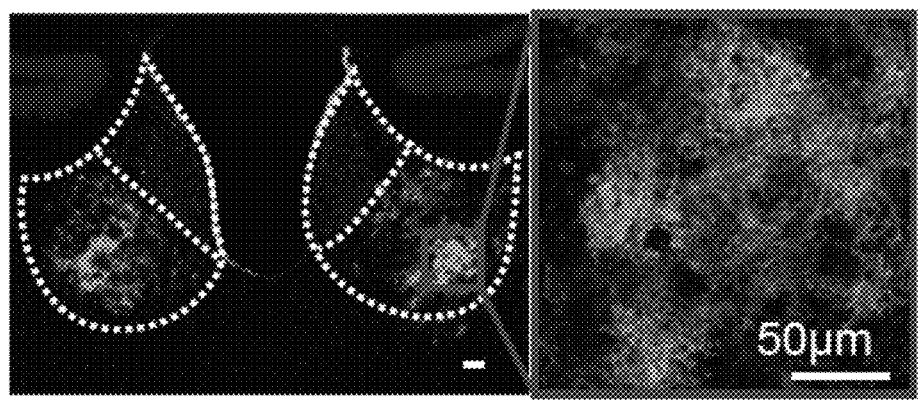
FIG. 5B

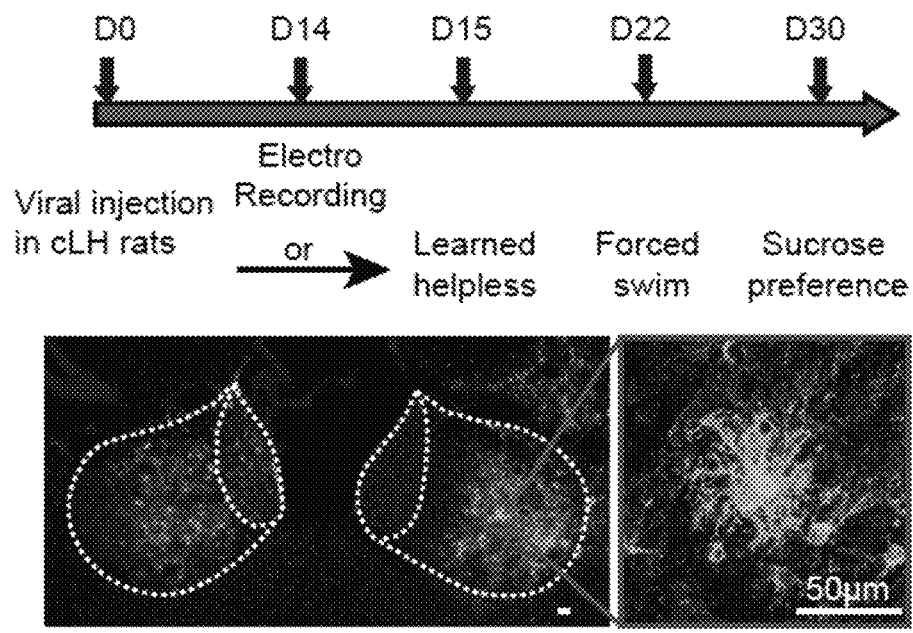
FIG. 6C
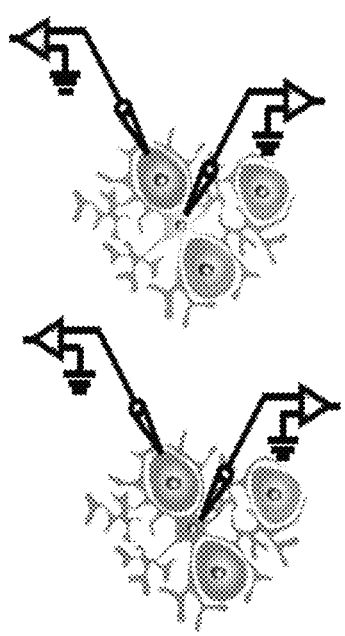 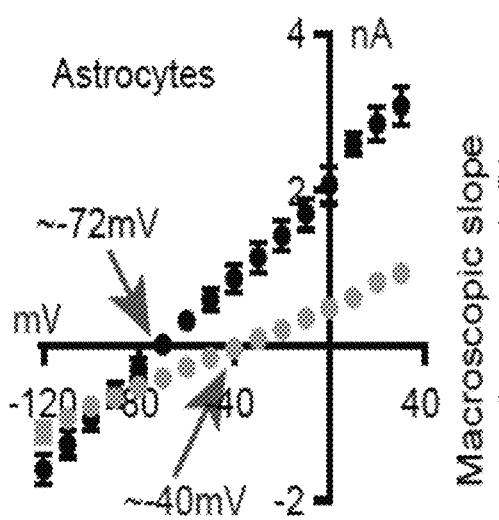 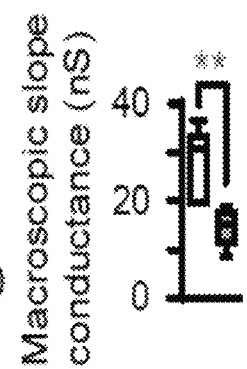
FIG. 6D                FIG. 6E

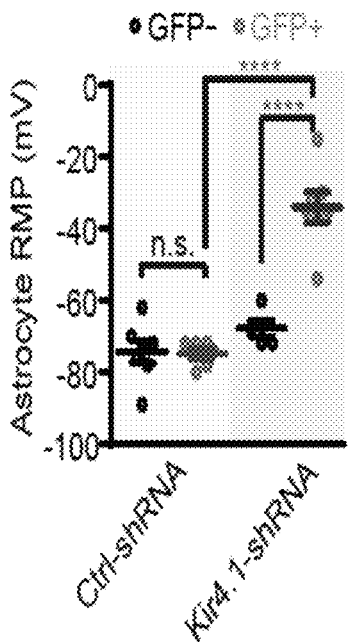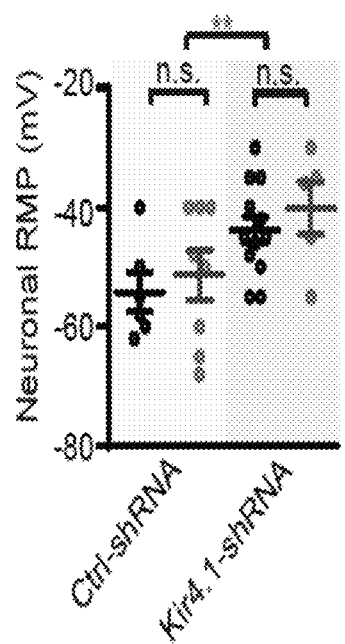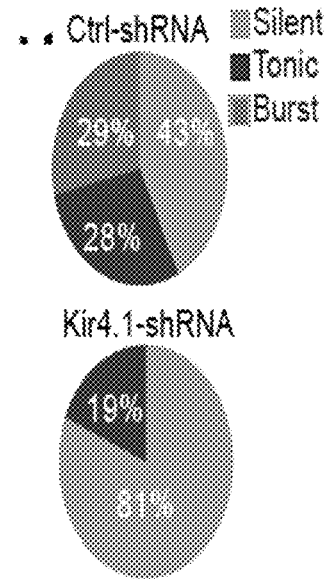
FIG. 6F    FIG. 6G    FIG. 6H
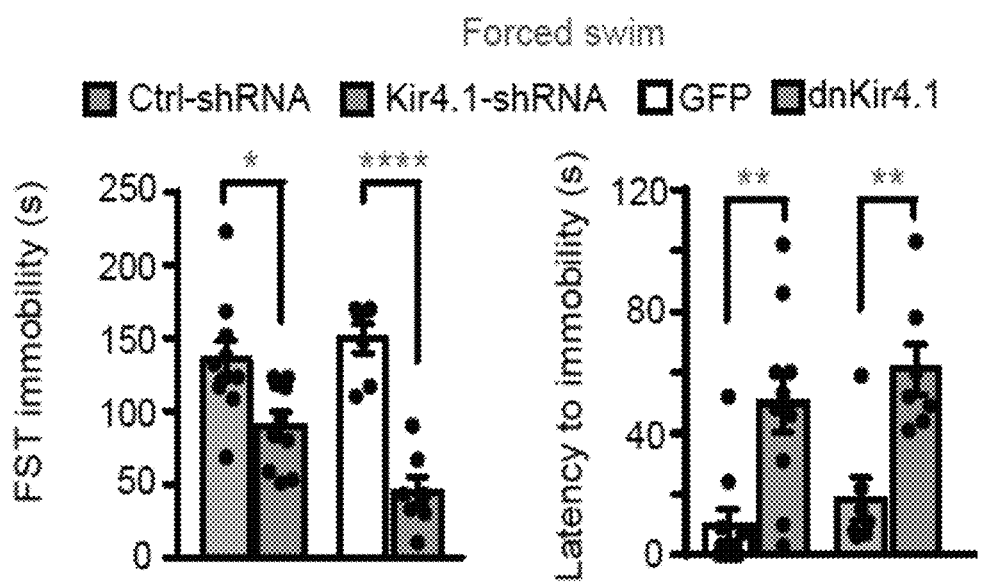
FIG. 6I

```
                                                                                    Section 1
                        (1)  1          10         20         30            49
 kir4.1-human-mRNA      (1)  ATGACGTCAGTTGCCAAGGTGTATTACAGTCAGACCACTCAGACAGAAA
   kir4.1-rat-mRNA     (1)  ATGACATCAGTTGCCAAGGTCTATTACAGCCAGACGACGCAGACAGAA
 kir4.1-mouse-mRNA     (1)  ATGACGTCGGTCGCTAAGGTCTATTACAGTCAGACGACTCAGACAGAA
          Consensus    (1)  ATGACGTCAGTTGCCAAGGTCTATTACAGTCAGACGACTCAGACAGAGA
                                                                                    Section 2
                        (50) 50         60         70         80            98
 kir4.1-human-mRNA     (50)  GCCGGCCCCTAATGGGCCCAGGGATACGACGGCGGAGAGTCCTGACAA
   kir4.1-rat-mRNA     (50)  GCCGGCCCCTAGTGGTCCAGGCATACGTCGGGAGGGTCCTGACAA
 kir4.1-mouse-mRNA     (50)  GCCGCCGCCTAGTGGCCCAGGCATACGCCGCGGAGGGTCCTCACGAA
          Consensus    (50)  GCCGGCCCCTAGTGGCCCCAGGAATACG GGAGGAGGGTCCTGACAAA
                                                                                    Section 3
                        (99) 99         110        120        130           147
 kir4.1-human-mRNA     (99)  AGATGGTCGGCAGCAAGGTGAGAATGGAGCAGATTGCCGACAAGCGCTTC
   kir4.1-rat-mRNA     (99)  AGACGGTCGAGCAAGGTGAGAATGGAGCATATTGCCGACAAGCGTTTC
 kir4.1-mouse-mRNA     (99)  AGACGGTCGGAGCAATGTGAGAATGGAGCAGATTGCCGACAAACGTTTC
          Consensus    (99)  AGATGGCCGGAGCAACGTGAGAATGGAGCACATTGCTGACAAGCGTTTC
                                                                                    Section 4
                        (148) 148        160        170        180          196
 kir4.1-human-mRNA    (148)  CTCTACCTCAAGGACTGTGGACAACCTTCATTGACATGCAGTGGCGCT
   kir4.1-rat-mRNA    (148)  CTCTACCTCAAGGACTGTGGACGACCTTCATTGACATGCAGTGGCGCT
 kir4.1-mouse-mRNA    (148)  CTCTACCTCAAGGACTGTGGAGACCTTCATTGACATGCAATGGCGCT
          Consensus   (148)  CTCTACCTCAAGGATCTATGGACGACCTTCATTGACATGCAGTGGCGCT
                                                                                    Section 5
                        (197) 197        210        220        230          245
 kir4.1-human-mRNA    (197)  ACAAGCTTCTGCTCTTCTCGGACCTTTGCAGGCACATGGTTCCTCTT
   kir4.1-rat-mRNA    (197)  ACAAGCTTCTGCTCTTCTCGGCGACCTTTGCAGGCACTTGGTTCCTCT
 kir4.1-mouse-mRNA    (197)  ACAAGCTTCTGCTCTTCTCTGCAACCTTTGCAGGCACGTGGTTCCTCT
          Consensus   (197)  ACAAGCTTCTGCTCTTCTCTGCAACCTTTGCAGGCAC TGGTTCCTCTT
                                                                                    Section 6
                        (246) 246        260        270        280          294
 kir4.1-human-mRNA    (246)  TGGCGTGGTGTGGTATCTGGTGGCTGTGGCACATGGGGACCTGCTGGAG
   kir4.1-rat-mRNA    (246)  TGGTGTGGTGTGGTATCTGGTCGCTGTGGCCACGGGGACCTGTTGGAG
 kir4.1-mouse-mRNA    (246)  TGGTGTGGTGTGGTATCTGGTGGCTGTGGCAGGGGACCTGTTGGAG
          Consensus   (246)  TGGCGTGGTGTGGTATCTGGTAGCTGTGGCCCATGGGGACCTGTTGGAG
                                                                                    Section 7
                        (295) 295   300        310        320        330    343
 kir4.1-human-mRNA    (295)  CTGGACCTCCGGCCAACCACAGCCCTGTGTGGTACAGGTGCACACA
   kir4.1-rat-mRNA    (295)  CTGGACCTCCGCCAACCACAGCCCTGTGTGTCAGGTGCACACA
 kir4.1-mouse-mRNA    (295)  CTGGACCTCCGCCAACCACAGCCCTTGTGTGGTGAGGTGCACACG
          Consensus   (295)  CTGGACCTCCTGCCAACCACACGCCCTGTGTGGTGCAGGTGCACACAC
                                                                                    Section 8
                        (344) 344   350        360        370        380    392
 kir4.1-human-mRNA    (344)  TCACTGGAGCCTTCCTCTTCTCCCTTGAATCCCAAACCACCATCGGCTA
   kir4.1-rat-mRNA    (344)  TTACCGGGAGCCTTCCTCTTCTCCCTCGAATCCAGACCACCATCGGCTA
 kir4.1-mouse-mRNA    (344)  TACCCGGAGCCTTCCTCTTCTCCCTGGAATCCAGACCACCATCGGCTA
          Consensus   (344)  TCACTGGAGCCTTCCTCTTCTCCCT GAATCCCAGACCACCATTGGCTA
```

FIG. 9A

```
                                                                                    Section 9
                    (393) 393       400       410       420       430       441
kir4.1-human-mRNA   (393) TGGCTTCCGCTACATCAGTGAGGAATGTCCCTGGCCATTGTGCTTCT
  kir4.1-rat-mRNA   (393) TGGCTTCCGCTACATCAGCGAGGAATGCCCTCTGGCCATGGTGCTTCTC
kir4.1-mouse-mRNA   (393) TGGCTTCCGCTACATCACGAGGAATGCCACTGGCCATCGTGCTTCTT
        Consensus   (393) TGGCTTCCGCTACATCAGTGAGGAATGCCCACTGGCCATTGTGCTTCTT
                                                                                    Section 10
                    (442) 442       450       460       470       480       490
kir4.1-human-mRNA   (442) ATTGCCCAGCTGGTGCTCACCACCATCCTGGAAATCTTCATCACGGTA
  kir4.1-rat-mRNA   (442) ATTGCACAGCTCGTGCTCACCACCATCCTGGAAATCTTCATCACGGAA
kir4.1-mouse-mRNA   (442) ATTGCGAGCTGGTGCTCACCACCATCTGGAAATCTTCATCACGGTA
        Consensus   (442) ATTGC CAGCTGGTGCTCACCACCATCCTGGAAATCTTCATCACAGGTA
                                                                                    Section 11
                    (491) 491       500       510       520       539
kir4.1-human-mRNA   (491) CCTTCCTGGCGAAGATTGCCCGGGCCAAGAAGCGGGCTGAGACCATTC
  kir4.1-rat-mRNA   (491) CCTTCCTTGCAAAGATTGCCCGGGCCAAAGAAGGGGCCGAGACGATTC
kir4.1-mouse-mRNA   (491) CCTTCCTTGCGAAGATTGCCCGGGCCTAAGAAGGGGCCGAGACGATCC
        Consensus   (491) CCTTCCTTGCAAAGATTGCCCGGCC AAGAAGAGGGCTGAGACGATCCG
                                                                                    Section 12
                    (540) 540       550       560       570       588
kir4.1-human-mRNA   (540) TTCAGCCAGCATGCAGTTGTGGCCAAATGGCAAGCCTGCCT
  kir4.1-rat-mRNA   (540) TTCAGCCAGCATGCGGTTGTGGCTACCAAAGGGAAGCTTGCCT
kir4.1-mouse-mRNA   (540) CTTCAGCCAGCATGCCGTTGTGGCTCCATAAGGGAAGCCTGCCTT
        Consensus   (540) TTTCAGCCAGCATGC GTTGTGGCTTCCACAACGGGAAGCCTTGCCTC
                                                                                    Section 13
                    (589) 589       600       610       620       637
kir4.1-human-mRNA   (589) ATGATCCGAGTGGCCAAGATGGCAAAAGGCCTCCTCATTGGCTGCCAGG
  kir4.1-rat-mRNA   (589) ATGATCCGGGTGCCCAACATGGCTAAGAGCTCCTCATTGGGTGCCAGG
kir4.1-mouse-mRNA   (589) ATGATCCGGCTGCCCAAGATGCGGAAGAGCTCCTCATTGGATGCCAGG
        Consensus   (589) ATGATCCGGGTTGCCAATATGCG AAGAGTCTCCTCATTGG TGCCAGG
                                                                                    Section 14
                    (638) 638       650       660       670       686
kir4.1-human-mRNA   (638) TGACAGGAAAACTGCTTTAGACCACCAAACCAAGGAAGGGAGAACAT
  kir4.1-rat-mRNA   (638) TGACAGGGAAACTGCTTCAAGCCACCACCAAGGAGGGAGAAAT
kir4.1-mouse-mRNA   (638) TGACAGGAAAACTGCTTCAACGCACCATACAAGGAGGGAGAAAT
        Consensus   (638) TGACAGGCAAACTGCTTCAAACCACCAGACAAAGGAGGGTGAGAATAT
                                                                                    Section 15
                    (687) 687       700       710       720       735
kir4.1-human-mRNA   (687) CGGCTCAACCAGGTCAAGTGACTTCCAAGTAGACACAGCCTCGA
  kir4.1-rat-mRNA   (687) TGGCTCAACCAGGTCAAGTGACTTCCAAGTAGACACAGCCTCGAT
kir4.1-mouse-mRNA   (687) TGGCTCAACCAGGTCAACGTGACTTCCAAGTAGACACAGCCTCAGA
        Consensus   (687) TCGGCTCAACCAGGTCAATGTGACTTTCCAAGTAGACACAGCCTCTGAC
                                                                                    Section 16
                    (736) 736       750       760       770       784
kir4.1-human-mRNA   (736) AGCCCCTTCCTTATTCTACCCCTTACCTTCTATCAGTGGTAGATGAGA
  kir4.1-rat-mRNA   (736) AGCCCCTTCTGATTCTACCCCTTACTTCTACCAGTGGTAGATGAGA
kir4.1-mouse-mRNA   (736) AGCCCCTTCTGATCCTACCCCTGACTTCTACACGTGGTAGATGAGA
        Consensus   (736) AGCCCCTTTCTCATTCTACCCCTGACTTTCTACCATGTGGTAGATGAGA
```

FIG. 9B

```
                                                                              Section 17
                  (785) 785      790       800       810       820      833
kir4.1-human-mRNA (785) CCAGTCCCTTGAAAGATCTCCCTCTTCGCAGTGGTGAGGGTGACTTTGA
  kir4.1-rat-mRNA (785) CCAGCCCCTTAAAGATCTCCCCCTCCGCAGCGGGGAGGGTGACTTCGA
kir4.1-mouse-mRNA (785) CCAGCCCCTTAAAGATCTCCCGCTCCGCAGCGGGGAGGGGACTTTGA
        Consensus (785) CCAGCCCCTTGAAAGATCTCCC CTCCGCAGTGGGGAGGGTGACTTTGA
                                                                              Section 18
                  (834) 834      840       850       860       870      882
kir4.1-human-mRNA (834) GCTGGTGCTGATCCTGAGTGGGACAGTGGAGTCCACCAGCGCCACCTG
  kir4.1-rat-mRNA (834) GCTCGTGCTGATCCTGAGTGGGACGGTGGAGTCCACCAGCGCCACCTG
kir4.1-mouse-mRNA (834) GCTGGTGCTGATCCTGAGTGGGACGGTGGAGTCCACCAGCGCCACCTGC
        Consensus (834) GCTGGTGCTGATCCTAAGTGGGACAGTGGAGTCCACCAGTGCCACCTGT
                                                                              Section 19
                  (883) 883      890       900       910       920      931
kir4.1-human-mRNA (883) CAGGTGCGCACTTCCTACCTGCCAGGAGATCCTTTGGGCTACGAGT
  kir4.1-rat-mRNA (883) CAGCTGCGCACTTCCTATCTGCCAGGAGATCCTTGGGCTACGAGT
kir4.1-mouse-mRNA (883) CAGGTGCGCACTTCCTACCTGCCAGGAGATCCTTGGGTTACGAGT
        Consensus (883) CAAGTTCGCACTTCCTACCTACCGGAGGAGATCCTCTGGGGCTACGAGT
                                                                              Section 20
                  (932) 932      940       950       960       970      980
kir4.1-human-mRNA (932) TCACACCTGCCATCTCACTGTCAGCCAGTGGTAAATACATAGCTGACTT
  kir4.1-rat-mRNA (932) TCACACCTGCTATCTCACTGTCAGCCAGTGGAAATACGTGGCTGACTT
kir4.1-mouse-mRNA (932) TCACGCCTGGGATCTCACTGTCAGCCAGTGGAAATACATAGCTGACTT
        Consensus (932) TCACACCTGC ATCTCACTGTCAGCCAGTGGCAAATACATAGCTGACTT
                                                                              Section 21
                  (981) 981      990       1000      1010      1020     1029
kir4.1-human-mRNA (981) TAGCCTTTTGACCAAGTTGTGAAAGTGGCCTCCCCAGTGGCCTCCGT
  kir4.1-rat-mRNA (981) AGCCTTTTGACCAAGTTGTGAAAGTGGCGTCCCGGTGGCTCCGA
kir4.1-mouse-mRNA (981) AGCCTTTTCGACCAAGTTGTGAAAGTGGCATCCGCAGTGGCTCCGC
        Consensus (981) CAGCCTTTTTGACCAGGTTGTGAAAGTGGC TCTCCAGTGGTCTCCG
                                                                              Section 22
                 (1030) 1030     1040      1050      1060      1070     1078
kir4.1-human-mRNA (1030) GACAGCACTGTACGCTACGGAGACCCTGAAAAGCTCAAGTTGGAGAGT
  kir4.1-rat-mRNA (1030) GATAGCACGGTACGTTAGGAGACCACGAAAAGCTCAAGTTGGAGAGT
kir4.1-mouse-mRNA (1030) GATAGCACCGTACGCTAGGAGACCCCGAGAAGCTCAAGTTGGAGAGT
        Consensus (1030) GATAGCACCGTACGCTATGGAGACCC GAAAAGCTCAAGTTGGAGAGT
                                                                              Section 23
                 (1079) 1079     1090      1100      1110      1120     1127
kir4.1-human-mRNA (1079) CATTAAGGAGCAAGCTGAGAAGGAGGCAGTGCCTTAGTGTGCGCAT
  kir4.1-rat-mRNA (1079) CATTAAGGAGCAAGCTGAAAGGAGGCAGTGCCCTTAGTGTGCGCAT
kir4.1-mouse-mRNA (1079) CATTAAGGAGCAAGCTGAAAGGAGGCAGTGCCCTTAGTGTGCGCAT
        Consensus (1079) CATTAAGAGAGCAAGCTGAAAAGGAAGGCAGTGCCCTTAGTGTGCGCAT
                                                                              Section 24
                 (1128) 1128     1140
kir4.1-human-mRNA (1128) CAGCAATGTCTGA
  kir4.1-rat-mRNA (1128) TAGTAACGTCTGA
kir4.1-mouse-mRNA (1128) CAGCAACGTCTGA
        Consensus (1128) CAGCAACGTCTGA
```

FIG. 9C

|  | (1) | 1 | 10 | 20 | 30 | 49 |
|---|---|---|---|---|---|---|
|  | (1) | - | - | - | - | - | human-kir4.1-protein (1)
mouse-kir4.1-protein (1)
rat-kir4.1-protein (1)
Consensus (1) MTSVAKVYYSQTTQTESRPLVAPGIRRRRVLTKDGRSNVRMEHIADKRF

(50) 50    60    70    80    98
(1) ---------------------------------------- human-kir4.1-protein (50)
mouse-kir4.1-protein (50)
rat-kir4.1-protein (50)
Consensus (50) LYLKDLWTTFIDMQWRYKLLLFSATFAGTWFLFGVVWYLVAVAHGDLLE

(99) 99    110    120    130    147
(1) ---------------------------------------- human-kir4.1-protein (99)
mouse-kir4.1-protein (99)
rat-kir4.1-protein (99)
Consensus (99) LGPPANHTPCVVQVHTLTGAFLFSLESQTTIGYGFRYISEECPLAIVLL (148) 148    160    170    180    196
(4) ---------------------------------------- human-kir4.1-protein (148)
mouse-kir4.1-protein (148)
rat-kir4.1-protein (148)
Consensus (148) IAQLVLTTILEIFITGTFLAKIARPKKRAETIRFSQHAVVASHNGKPCL (197) 197    210    220    230    245
(4) ---------------------------------------- human-kir4.1-protein (197)
mouse-kir4.1-protein (197)
rat-kir4.1-protein (197)
Consensus (197) MIRVANMRKSLLIGCQVTGKLLQTHQTKEGENIRLNQVNVTFQVDTASD (246) 246    260    270    280    294
(4) ---------------------------------------- human-kir4.1-protein (246)
mouse-kir4.1-protein (246)
rat-kir4.1-protein (246)
Consensus (246) SPFLILFLTFYHVVDETSPLKDLPLRSGEGDFELVLILSGTVESTSATC (295) 295    300    310    320    330    343
(4) ---------------------------------------- human-kir4.1-protein (295)
mouse-kir4.1-protein (295)
rat-kir4.1-protein (295)
Consensus (295) QVRTSYLPEEILWGYEFTPAISLSASGKYIADFSLFDQVVKVASPSGLR (344) 344    350    360    370    380
(4) ---------------------------------------- human-kir4.1-protein (344)
mouse-kir4.1-protein (344)
rat-kir4.1-protein (344)
Consensus (344) DSTVRYGDPEKLKEESLREQAEKEGSALSVRISNV

USE OF POTASSIUM CHANNEL INHIBITOR FOR TREATING DEPRESSION

CROSS-REFERENCE TO RELATED PATENT APPLICATIONS

The present application is a continuation of International Patent Application No. PCT/CN2018/086021 filed May 8, 2018, which claims priority to Chinese Patent Application No. 201710322245.X, filed May 9, 2017, which are hereby incorporated into the present application by reference in their entirety.

REFERENCE TO SEQUENCE LISTING SUBMITTED ELECTRONICALLY

The content of the electronically submitted sequence listing, with the file name SeqList-KChannInhibitor-Updated-ST25.txt, size 17,421 bytes, and date of creation Jan. 15, 2020, filed herewith, is incorporated herein by reference in its entirety.

TECHNICAL FIELD OF THE INVENTION

The present disclosure relates generally to the field of disease therapy and pharmacy field, and in particular, provides a method for treating depression and pharmaceutical compositions for treating depression and the method for manufacturing it.

BACKGROUND OF THE INVENTION

Depression is a chronic mental disorder characterized by significant and persistent low mood, lack of motivation, behavioral despair, and loss of pleasure. Patients with depression may even show suicidal tendency.

Lateral habenula (LHb) has been considered as a key brain area for studying the pathophysiology of depression in recent years. Significant elevation of lateral habenular neurons activity has been found in many animal models of depression and patient of depression.

Abnormal neuron activities are mainly attributed to the dysfunction of synaptic transmission and changes in their physiological characteristics and the surrounding of neurons. Astrocytes are involved in regulating the activity of neurons, the release of transmitters, and play an important role in mental diseases, including schizophrenia, epilepsy, Alzheimer's disease, and depression (Hamilton et al., 2010). The postmortem brain studies found that the density, morphology and function of glial cell in frontal limbic system significantly changed in major depressive disorder compared with controls (Cotter et al., 2001; Coyle et al., 2000; Rajkowska et al., 2007). Astrocyte apoptosis by chemical drugs is sufficient to cause depressive symptoms (Banasr et al., 2008). Antidepressant drugs can act directly on astrocytes, significantly affecting their morphology and function, which have been proposed as one of the antidepressant mechanisms (Czeh et al., 2013). These evidence suggests that in addition to neurons, glial cells also play an important role in mental disease.

The inward rectifier-type potassium channel (Kir) is a hyperpolarization-activated potassium channel, which includes 7 families, Kir1-Kir7. The same kind of Kir channel can be divided into a variety of subtypes due to the existence of splicing variance. The Kir channel distributes in heart, kidney, nervous system and other tissues and organs. Kir4.1 (also known as potassium voltage-gated channel subfamily J member 10, Kcnj10) is an astrocyte expressed inwardly rectifying potassium channel, mainly responsible for setting the astrocytic RMPs and buffering the excess extracellular $K^+$ in synaptic microdomains. Dysfunction of Kir4.1 will greatly affect the function of glial cells and neurons and contribute to many diseases. In mammals, both the Kir4.1 protein sequence and the coding nucleic acid sequence are conservative.

There are some existing antidepressants in the field, but these drugs usually take effect after a long period of time. Almost all known existing antidepressants in the field typically take a week to several weeks to be capable of exerting antidepressant effects. For example, the commonly used 5-HT reuptake inhibitors (SSRI) are usually effective in 2-3 weeks; 5-HT and serotonin and norepinephrine reuptake inhibitors are usually only effective after 1 week. Moreover, the pathological mechanism leading to depression has not been fully recognized. There is a need in the art for new methods and drugs for treating depression, which have a faster onset rate or a safer effective dosage.

SUMMARY OF THE INVENTION

The inventors of the present disclosure have, for the first time and unexpectedly, found that Kir4.1 present in astrocytes of the lateral habenula (also known as LHb) is a crucial regulatory factor of depression (Cui et al. 2018). With the assistance of molecular, behavioral and electrophysiological methodologies, the inventors found out that Kir4.1 expressed in astrocytes of the lateral habenula is presented in a form that closely surrounds the cells of habenula neurons. Kir4.1 regulates the extracellular potassium balance and affects the discharging characteristics of the lateral habenula neurons, which leads to over-hyperactivity of the lateral habenula, in turn affecting the phenotype of depression. The inventors of the present disclosure have also discovered and demonstrated various pharmaceutical agents that are capable of inhibiting, depressing, or blocking the expression level or the functionality of Kir4.1 in the lateral habenula, and have thus provided a method and a medicament (i.e. pharmaceutical composition) for treating (suppressing) depression by inhibiting the activity of Kir4.1.

In particular, based on the above discoveries, the present disclosure provides a method for treating depression in a subject substantially through the inhibition of the activity of Kir4.1, and more specifically by use of Kir4.1 inhibitors for obtaining medicaments or pharmaceutical compositions for treating depression. The present disclosure also provides a pharmaceutical composition comprising a pharmaceutical agent capable of inhibiting the activity of Kir4.1 for treating depression, and further provides a formulation thereof allowing for local administration in lateral habenula and for systemic administration as well.

According to some embodiments of the disclosure, the pharmaceutical agent (i.e. Kir4.1 inhibitor) comprises a small molecule compound which upon administration in an appropriate manner, can inhibit the activity of Kir4.1 functionality. According to some preferred embodiments of the disclosure, the pharmaceutical agent is a selective Kir4.1 inhibitor. Herein, a "selective Kir4.1 inhibitor" is generally referred to as a Kir4.1 inhibitor that has no inhibitory activity against other Kir proteins, or has a significantly less inhibitory activity against other Kir proteins in compassion with that against Kir4.1, for example the inhibitory activity against other Kir proteins is 50% or less, preferably 20% or less, more preferably 5% or less, than the inhibitory activity against Kir4.1.

Herein optionally, such Kir4.1-inhibiting small molecule compound can be a selective serotonin reuptake inhibitor (SSRIs) (e.g. fluoxetine, sertraline, and fluvoxamine, etc.) or a tricyclic antidepressants (TCAs) (e.g. nortriptyline, amitriptyline, desipramine and imipramine, etc.) which have been shown to also inhibit Kir4.1, yet with lower affinity (Ohno et al., 2007; Wang et al., 2006). A highly selective and specific Kir4.1 inhibitor, VU0134992, has also been reported (Kharade et al., 2018). These Kir4.1-inhibiting small molecule pharmaceutical agents can be administered to a subject with depression either in a local manner (i.e. direct drug delivery to the LHb of the subject) or in a systemic manner.

According to some other embodiments of the present disclosure, the Kir4.1 inhibitor is a small interfering RNA or a precursor thereof which suppresses expression of Kir4.1. RNA interference (RNAi) induces efficient and specific degradation of homologous mRNA with double-stranded RNA (dsRNA), thereby reducing or even eliminating the expression of the target gene. In the present disclosure, the interfering RNA may include small interfering RNA (siRNA), short hairpin RNA (shRNA), and/or microRNA (miRNA). One way to administer interfering RNA in vivo is to administer a shRNA (siRNA precursor), such as a short hairpin RNA comprising two short inverted repeats. The siRNA sequence was cloned into a plasmid vector as a "short hairpin". When introduced into cells, the hairpin sequence is expressed to form a "double-stranded RNA", and the corresponding siRNA is generated by the intracellular Dicer enzyme to exert RNA interference.

According to different embodiments of the present disclosure, the small interfering RNA or a precursor thereof used in the present disclosure has identical or complementary sequence with the target mRNA of Kir4.1, or have at least 90% homology with the identical or complementary sequence. For example, according to some embodiments of the present disclosure, said small interfering RNA or a precursor thereof which suppresses expression of Kir4.1 can comprise one of the following sequences, which are also the target sequences in the Kir4.1 mRNA sequence:

5'-GGACGACCTTCATTGACAT-3'; (SEQ ID No. 1)

5'-GCTACAAGCTTCTGCTCTTCT-3'; (SEQ ID No. 2)

5'-GCTCTTCTCGCCAACCTTTAC-3'; (SEQ ID No. 3)

5'-CCGGAACCTTCCTTGCAAA-3'; (SEQ ID No. 4)

5'-GCGTAAGAGTCTCCTCATTGG-3'; or (SEQ ID No. 5)

5'-GCCCTTAGTGTGCGCATTA-3'. (SEQ ID No. 6)

The above interfering RNA or its precursor targets the sequences of the corresponding mRNA fragments of the rat Kir4.1, whose sequence is set forth in SEQ ID No. 7 (i.e., the CDS region of Genebank No. NM_031602.2). In other words, the sequence of the interfering RNA having one of the target sequences as set forth in SEQ ID No. 1-6 is identical or complementary to the sequence of the mRNA fragments of rat Kir4.1, or has a homology of more than 90% identical thereto or complementary therewith. People of ordinary skills in the field will understand and be able to obtain fragments of an interfering RNA sequence of the Kir4.1 correspondingly in other mammals (e.g., human, mouse, and the like).

According to some embodiments of the present disclosure, the Kir4.1 inhibitor is a mutant Kir4.1 protein with diminished or totally deactivated potassium channel activity or an nucleotide sequence or nucleic acid sequence encoding said mutant Kir4.1 protein. A mutant protein can compete with the wide-type protein, thereby reducing the activity or the functionality of the wide-type protein. The mutant protein can be expressed in a target tissue or cell by administering a vector expressible in a target tissue or cell (i.e. the vector carries an expressible mutant protein gene and/or an expression factor thereof). According to some more specific embodiments of the disclosure, the mutant Kir4.1 protein is a mutant Kir4.1 protein with one or more mutations in the channel pore region of Kir4.1. Optionally, said mutant Kir4.1 protein can have one or more mutations at GYG corresponding to position 130-132 of the amino acid sequence of wild-type Kir4.1 protein as set forth in SEQ ID NO. 8, for example, said GYG can be mutated to be AAA. Kir4.1 having the amino acid sequence of SEQ ID No. 8 is Kir4.1 (NP_113790.2) of rat. People of ordinary skills in the art can, based on known reports (e.g., Hiroshi et al., 2010) and understanding on the conservativeness of the sequence of Kir4.1, obtain information of the channel pore region of Kir4.1 of other mammals and introduce mutations to Kir4.1 in the channel pore region thereof.

According to some embodiments of the present disclosure, the Kir4.1 inhibitor is a therapeutical antibody against Kir4.1, including a polyclonal antibody or a monoclonal antibody.

These above Kir4.1-inhibiting biological pharmaceutical agents (i.e. non-small molecule agents such as interfering macromolecules including RNAs or mutant DNAs or antibodies) can be administered to a subject with depression either in a local manner (i.e. direct delivery to the LHb of the subject) or in a systemic manner.

Certain compounds are known in the art for use in the treatment of depression, which include, for example, buspirone, mianserin, fluoxetine, sertraline, fluvoxamine or nortriptyline. However, in these reports, the anti-depression mechanisms that have been discovered or presumed are completely different from the mechanism discovered by the present disclosure, that is, Kir4.1 present in astrocytes of the lateral habenula plays an important role in the treatment of depression by inhibiting the abnormal firings, and particularly the abnormal burst firings, of lateral habenula neurons. Without affecting the novelty and inventive steps of the present disclosure, in one aspect of the present disclosure, in the method, the use of Kir4.1 inhibitor in obtaining a medicament, and the pharmaceutical composition for treating depression by means of inhibiting Kir4.1 as disclosed herein, the Kir4.1 inhibitor does not include buspirone, mianserin, fluoxetine, sertraline, fluvoxamine or nortriptyline. Further without affecting the novelty and inventive steps of the present disclosure, in the method, the use of Kir4.1 inhibitor in obtaining a medicament, and the pharmaceutical composition for treating depression by means of inhibiting Kir4.1 as disclosed herein, said Kir4.1 inhibitor is not a selective serotonin reuptake inhibitors (SSRIs) or tricyclic antidepressants (TCAs).

In the present disclosure, the term "depression" can be referred to as lateral-habenula-mediated depression, and in more particular, may be referred to as lateral-habenula-burst-mediated depression. The inventors of the present application have found and demonstrated that the abnormal firing of neurons in the lateral habenula, especially the abnormal burst firing plays an important role in the generation of depression. The inventors of the present application have found and demonstrated that Kir4.1 is a crucial regulatory factor on burst firing, thus can be a crucial regulatory factor of depression. The inventors of the present application have also identified and proved different types of Kir4.1 inhibitors. The inventors of the present application hereby provide methods and medicaments for treating depression. This is a pathological mechanism containing the target tissue in the brain and the molecular targets that currently known mechanisms and drugs have failed to target. Accordingly, the method, the pharmaceutical agent, or the pharmaceutical composition provided by the present disclosure are particularly suitable for use in the depression patients to whom the above-described anti-depression methods and drug are ineffective.

According to some embodiments of the present disclosure, the method and the pharmaceutical agent or medicament for treating depression are configured for use in lateral habenula locally (i.e. configured to be locally administered to the lateral habenula). For methods and medicaments/agents used on nerve tissues, particularly the nerve tissues in the brain, such as on the lateral habenula, it is beneficial to limit the effects of the drug/medicament/pharmaceutical agent to the target tissue. The administration of a medicine locally in the lateral habenula is a limiting technical feature to a method and a pharmaceutical agent for treating depression. In any method or pharmaceutical agent or medicament for LHb, whether the method or drug can take effects in LHb shall be considered, including whether the drug can reach LHb, and whether the effective concentration can be achieved in LHb, etc. According to some embodiments of the present disclosure, the medicament or pharmaceutical composition has a dosage form for local administration to the lateral habenula. The action of the medicament can be limited to the target tissue by local administration, for example by formulating the medicament as a dosage form that can be administered locally to the lateral habenula by cannulation. In another example, the drug is formulated in a dosage form having a sustained release after being administered or delivered into the tissue. The above medicaments can also be formulated in the form of tissue-specific targeted drug delivery systems. For example, a small molecule compound or a biologically active molecule (nucleic acid such as a protein-encoding DNA or mRNA molecule, or a protein such as an antibody, etc.) capable of specifically binding to a protein expressed in the lateral habenula can be used to link with an antibody or fragments thereof which binds to cells of the lateral habenula to form a complex molecule capable of recognizing and binding to lateral habenula.

According to some embodiments of the present disclosure, in the method for treating depression by inhibiting Kir4.1 in the lateral habenula and the use of a Kir4.1 inhibitor as a pharmaceutical agent for treating depression which is locally administered in the lateral habenula, said Kir4.1 inhibitor can comprise a Kir4.1-inhibiting small molecule compound or a pharmaceutically acceptable formula thereof. Herein the Kir4.1-inhibiting small molecule compound or the a pharmaceutically acceptable formula thereof can be a selective serotonin reuptake inhibitor capable of inhibiting Kir4.1 activity (e.g. fluoxetine, sertraline, and fluvoxamine, etc.) or a tricyclic antidepressant capable of inhibiting Kir4.1 activity (e.g. nortriptyline, amitriptyline, desipramine and imipramine, etc.), or can be a selective Kir4.1 inhibitor (such as VU0134992).

In another aspect, the present disclosure also provides a pharmaceutical composition for treating depression, comprising a therapeutically effective amount of Kir4.1 inhibitor, which is substantially the pharmaceutical agent in the pharmaceutical composition, wherein said Kir4.1 inhibitor is as defined and described above.

According to some embodiments of the present disclosure, in the pharmaceutical composition for treating depression, the Kir4.1 inhibitor is a small interfering RNA or a precursor thereof which suppresses expression of Kir4.1. In one aspect of the present disclosure, the small interfering RNA or a precursor thereof used in the present disclosure has identical or complementary sequence with the target mRNA of Kir4.1, or have at least 90% homology with the identical or complementary sequence. For example, according to some embodiments, said small interfering RNA or a precursor thereof which is capable of suppressing expression of Kir4.1 has one of the following sequences:

5'-GGACGACCTTCATTGACAT-3'; (SEQ ID No. 1)

5'-GCTACAAGCTTCTGCTCTTCT-3'; (SEQ ID No. 2)

5'-GCTCTTCTCGCCAACCTTTAC-3'; (SEQ ID No. 3)

5'-CCGGAACCTTCCTTGCAAA-3'; (SEQ ID No. 4)

5'-GCGTAAGAGTCTCCTCATTGG-3'; or (SEQ ID No. 5)

5'-GCCCTTAGTGTGCGCATTA-3'. (SEQ ID No. 6)

According to some embodiments of the present disclosure, in the pharmaceutical composition for treating depression, the Kir4.1 inhibitor can be a mutant Kir4.1 protein with diminished or deactivated potassium channel activity, or can be an encoding nucleotide sequence thereof. Optionally, the mutant Kir4.1 protein can be a mutant Kir4.1 protein with a mutation in the channel pore region of Kir4.1. Furthermore, said mutant Kir4.1 protein can have a mutation in GYG at positions 130-132 of the amino acid sequence as set forth in SEQ ID NO. 8. For example, said GYG can be mutated to be AAA.

According to some embodiments of the present disclosure, in the pharmaceutical composition for treating depression, the Kir4.1 inhibitor can be a specific antibody against Kir4.1, including a polyclonal antibody or a monoclonal antibody.

Without affecting the novelty and inventive steps of the present disclosure, according to some embodiments of the present disclosure, in the pharmaceutical composition for treating depression, said Kir4.1 inhibitor does not include buspirone, mianserin, fluoxetine, sertraline, fluvoxamine or nortriptyline, and the like. Without affecting the novelty and inventive steps of the present disclosure, according to some embodiments of the present disclosure, in the pharmaceutical composition for treating depression, said Kir4.1 inhibitor is not a selective serotonin reuptake inhibitors (SSRIs) or tricyclic antidepressants (TCAs).

The pharmaceutical composition for treating depression provided by the present disclosure are particularly suitable for treating depression patients to whom the other anti-depression methods and drug are ineffective.

According to some embodiments of the present disclosure, the pharmaceutical composition for treating depression are configured for local administration in lateral habenula. For example, said pharmaceutical composition can be in a formulation that is locally administered in lateral habenula. For these locally administered pharmaceutical composition for treating depression disclosed herein, said Kir4.1 inhibitor can include a selective serotonin reuptake inhibitor (such as buspirone, mianserin, fluoxetine, sertraline, fluvoxamine) or tricyclic antidepressants (such as nortriptyline).

In summary of the above, in a first aspect of the present disclosure, a pharmaceutical composition for treating depression in a subject, especially in a mammal subject (e.g. a rat, a mouse, or a human), is provided. The pharmaceutical composition comprises a therapeutically effective amount of a pharmaceutical agent (i.e. the active component in the pharmaceutical composition). The pharmaceutical agent is capable of, upon administration to the subject, suppressing an expression, interfering with a function, or inhibiting an activity, of an astroglial potassium channel in a lateral habenula (LHb) of the subject such that bursting activity of neurons in the lateral habenula (LHb) of the subject is suppressed.

According to some embodiments of the pharmaceutical composition, the pharmaceutical agent, if in a therapeutically effective amount, is capable of suppressing an expression, interfering with a function, or inhibiting an activity, of Kir4.1 in a lateral habenula (LHb) of the subject in a selective manner. Herein "selective manner" is referred to as a situation that only Kir4.1 is inhibited or suppressed by the pharmaceutical composition without noticeable inhibitory effects on other inward rectifier potassium channel family members.

According to some embodiments of the pharmaceutical composition disclosed herein, the pharmaceutical agent is capable of suppressing an expression or interfering with a function of Kir4.1 in astrocytes in the lateral habenula (LHb) of the subject to thereby inhibit the activity of the astroglial potassium channel in the subject.

Optionally, the pharmaceutical agent can comprise a recombinant vector, such as a recombinant viral vector (e.g. recombinant adeno-associated virus (AAV) vector), that is configured to express in the astrocytes in the lateral habenula of the subject biological molecules capable of suppressing the expression, or block the function, of Kir4.1.

According to some embodiments, the biological molecules comprise RNA molecules that are capable of suppressing or silencing the expression of Kir4.1 through RNA interference (RNAi), and as such, the RNA molecules can comprise at least one of a short hairpin RNA (shRNA) molecule, a small interfering RNA (siRNA) molecule, a micro-RNA (miRNA) molecule, or an antisense RNA molecule.

According to certain specific embodiments, the RNA molecules comprise a shRNA molecule, which comprises two complementary sequences, and one of the two complementary sequences has a nucleotide sequence that is substantially identical to a sequence as set forth in any one of SEQ ID NOS. 1-6.

Preferably, the one of the two complementary sequences has a nucleotide sequence that is identical to the sequence as set forth in SEQ ID NO. 2. Such a shRNA can be universally used to suppress or silent the expression of Kir4.1 to thereby be employed in the pharmaceutical composition for treating depression in mammals like human, since the target sequence of this particular shRNA in the Kir4.1 mRNA sequence is 100% identical across rat, mouse and human.

Preferably in the pharmaceutical composition, the recombinant vector can be a recombinant viral vector capable of preferentially or specifically targeting the astrocytes of the subject, such as based on an adeno-associated virus (AAV) of 2/5 serotype (AAV2/5).

According to some embodiments, the recombinant vector includes a promoter that is operably connected to, and configured to drive an astrocyte-specific expression of, a functional sequence to thereby generate the biological molecules. Herein the functional sequence can be the above mentioned Kir4.1-targeting shRNA, or a dominant negative mutant Kir4.1, which will also be described below. The promoter can optionally be a human GFAP (gfaABC1D) promoter.

According to some embodiments of the pharmaceutical composition, the biological molecules comprise polypeptide molecules that are capable of inhibiting the function of Kir4.1, such as a mutant Kir4.1 protein that is capable of interfering with the function of Kir4.1 in a dominant negative manner. Herein, optionally the mutant Kir4.1 protein comprises a sequence alteration at a channel core region of a Kir4.1 protein of the subject. The sequence alteration can be preferably at a GYG segment corresponding to position 130-132 of the Kir4.1 protein as set forth in any one of SEQ ID NOS. 8, 16 or 18 (i.e. corresponding to rat, mouse and human Kir4.1 protein sequences respectively). According to one specific embodiment, the sequence alteration comprises a GYG-to-AAA point mutation.

According to some embodiments of the pharmaceutical composition, the pharmaceutical agent comprises a small molecule agent capable of inhibiting the activity of the astroglial potassium channel in the astrocytes in the lateral habenula of the subject. Herein optionally, the small molecule agent can be a Kir4.1-inhibiting selective serotonin reuptake inhibitor (SSRIs) (e.g. fluoxetine, sertraline, and fluvoxamine, etc.) or a Kir4.1-inhibiting tricyclic antidepressants (TCAs) (e.g. nortriptyline, amitriptyline, desipramine and imipramine, etc.), and more preferably, can be a highly selective Kir4.1 inhibitor VU0134992.

In a second aspect, the present disclosure further provides a method for treating depression in a subject. The method comprises: administering to the subject a pharmaceutical composition according to any one of the embodiments as described above.

According to some embodiments, the pharmaceutical agent in the pharmaceutical composition comprises a recombinant viral vector configured to express in the astrocytes in the lateral habenula of the subject biological molecules capable of suppressing the expression, or block the function, of Kir4.1, and as such, the step of administering to the subject a pharmaceutical composition comprises:

obtaining virus particles carrying the recombinant viral vector; and the virus particles to the subject.

Optionally, the administering the virus particles to the subject can be through an injection or an inhalation, or another practical administration method.

According to some other embodiments, the pharmaceutical agent in the pharmaceutical composition comprises a small molecule agent capable of inhibiting the activity of the astroglial potassium channel in the astrocytes in the lateral habenula of the subject. As such, the step of administering to the subject a pharmaceutical composition comprises:

administering the pharmaceutical composition in a systemic manner; or administering the pharmaceutical composition locally to the lateral habenula of the subject.

In particular embodiments, the present disclosure provides a pharmaceutical composition comprising a virus particle of the invention in a pharmaceutically-acceptable carrier or other medicinal agents, pharmaceutical agents, carriers, adjuvants, diluents, etc. For injection, the carrier will typically be a liquid. For other methods of administration, the carrier may be either solid or liquid, such as sterile, pyrogen-free water or sterile pyrogen-free phosphate-buffered saline solution. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

In other embodiments, the present invention provides a pharmaceutical composition comprising a cell in which an AAV provirus is integrated into the genome in a pharmaceutically-acceptable carrier or other medicinal agents, pharmaceutical agents, carriers, adjuvants, diluents, etc.

Herein, by "pharmaceutically acceptable" it is meant a material that is not biologically or otherwise undesirable, e.g., the material may be administered to a subject without causing any undesirable biological effects. Thus, such a pharmaceutical composition may be used, for example, in transfection of a cell ex vivo or in administering a viral particle or cell directly to a subject.

In yet another aspect, the present disclosure also provides an animal model of depression, which can be a rat or a mouse. The animal model of depression provided herein shows symptoms of depression, and has overexpressed Kir4.1 in the lateral habenula.

In yet another aspect, the present disclosure further provides a method for screening potential substances for treating depression using the animal model of depression as described above. The screening method comprises the steps of:

(1) adding a test substance to be screened to an in vitro testing system;

(2) checking an expression level and/or an activity of Kir4.1 in an in vitro testing system in the testing group; comparing it with the control group.

Wherein, if the symptoms associated with depression in the animal model of depression are significantly improved, it indicates that the test substance is a potential substance that can be used to treat depression.

In yet another aspect of the present disclosure, said method further comprises one or more if the following steps:

further testing the effect of the test substance on the burst in neuron; and/or administering said test substance to an animal model of depression and observing how it affects the symptoms associated with depression.

Wherein, in comparison with the negative control group, if the expression level of Kir4.1 is significantly decreased, and/or the Kir4.1 channel activity is significantly decreased, it indicates that the test substance is a potential substance that can be used to treat depression.

In still another aspect of the disclosure, the method of screening for a potential substance for treating depression further comprises one or more of the following steps:

the potential substances screened in the previous step are further tested for their effects on the burst in neurons; and/or the potential substances screened in the previous step are administered to animal models to observe their effects on the symptoms of depression.

When testing the effect on the burst in neurons, if the ratio of burst in neurons in the test group to which the test substance was added or administered is significantly lower than that of the negative control group (or the blank control group), it means that test substances are potential substances for the treatment of depression.

In yet another aspect, the present disclosure also provides a method of diagnosing depression, comprising detecting the expression of Kir4.1 in the lateral habenula of the patient. According to some embodiments, the method of diagnosing depression comprises: detecting an increase in expression of Kir4.1 in the lateral habenula of a subject (such as a human patient). According to some more specific embodiments, the method of diagnosing depression comprises: comparing the expression of Kir4.1 in lateral habenula of the patient at different timings (for example, at different stages of depression, or before or after treatment), or comparing the expression of Kir4.1 in the lateral habenular of a normal subject to that in a general or a specific population. If the expression of Kir4.1 is significantly increased, the subject is diagnoses to have depression.

In one aspect of the disclosure, expression of Kir4.1 can be detected by any methods known in the art for detecting protein (expression) in a sample. The methods can identify the presence or absence of Kir4.1. The methods can also quantitatively detect the amount of expression of Kir4.1.

Methods for detecting a protein (expression) in a sample which can be used in the present disclosure include immunoassay. For example, ELISA or Western blotting carried out with an antibody that specifically recognizes Kir4.1, in which the antibodies can be monoclonal or polyclonal antibodies.

Methods for detecting a protein (expression) in a sample can be used in the present disclosure further comprises detecting the presence or amount of mRNA of Kir4.1, for example, detecting the amount of mRNA of Kir4.1 or a fragment thereof in the sample by RT-PCR.

According to some embodiments of the disclosure, the test sample is from the lateral habenular of the subject. Optionally, the test sample is from an ex vivo sample. Optionally, detection of the expression of Kir4.1 can also be performed by in vivo observation and detection of the amount of Kir4.1 of the lateral habenular of the subject. For example, the test includes imaging the lateral habenular of the patient, for example PET imaging. The positron emission tomography (PET) scan of the lateral habenular is carried out by intravenous injection of positron emission radionuclide tracer which recognizes and displays Kir4.1, and followed by a positron emission tomography (PET) scan.

Throughout the disclosure, the following terms are defined.

The subject to whom the method is applied and the pharmaceutical composition is administered as described in the present disclosure can be a mammal, including a human or a non-human primate such as a monkey. The mammal can be other animals such as rats, mice, rabbits, pigs, dogs, and the like. The mammal can be a domestic animal such as a cat or a dog.

Herein, the term "pharmaceutical agent", "therapeutic agent", or "agent", or alike, that is capable of inhibiting Kir4.1 can be referred to as an agent which can decrease or eliminate Kir4.1 channel activity, and the Kir4.1 channel activity is referred to as a functionality of Kir4.1 that allows potassium ions to pass through cell membrane. Kir4.1 regulates the potassium ion concentration of the external fluid around the nerve cells and transports excess extracellular potassium ions to buffer the extracellular environment and control the resting membrane potential level, thereby affecting the physiological activity of the nervous system.

Notably, a pharmaceutical agent capable of inhibiting Kir4.1 may comprise a compound, a composition, or a mixture that can decrease or eliminate the Kir4.1 channel activity, and may optionally comprise an agent or a reagent that is used in the method for inhibiting Kir4.1 activity (including a surgical method), and the like. Further optionally, the pharmaceutical agent capable of inhibiting Kir4.1 may be an agent which can affect the protein level and/or the protein activity of Kir4.1, so as to affect the Kir4.1 channel activity. The pharmaceutical agent as such can be of an entity of a small molecule compound or composition, or can be of an entity of an active macromolecule such as a protein or a nucleic acid. For example, the pharmaceutical agent can be an antagonist such as an antibody that directly binds to and negatively modulates the functionality of, Kir4.1, or can be a nucleic acid that directly affects the expression level of Kir4.1, or optionally can further be a protein/nucleic acid that indirectly modulates the expression level and/or functionality of Kir4.1. These protein agents or nucleic acid agents can be delivered to a target tissue or cell by techniques well known in the art, for example, in conjunction with a suitable expression vector.

Throughout the disclosure, the term "Kir4.1", or "inward rectifier potassium channel Kir4.1", is also known as potassium voltage-gated channel subfamily J member 10 (Kcnj10). Kir4.1 is a member of inward rectifier potassium channel. Kir4.1 in neurogliocytes allows potassium ions to pass through cell membrane. Kir4.1 regulates the potassium ion concentration of the external fluid around the nerve cells and transports excess extracellular potassium ions to buffer the extracellular environment and control the resting membrane potential level, thus affecting the physiological activity of the nervous system. In mammals, the amino acid sequence of Kir 4.1 and the nucleotide sequence encoding it are both very conservative. Gene encoding human Kir4.1 (NP_002232) is KCNJ10 (Ensembl: ENSG00000177807). Gene encoding rat Kir4.1 (NP_113790) is KCNJ10 (Ensembl: ENSMUSG00000044708).

As used herein and throughout the disclosure, the term "treatment" can be interpreted to include a process or an outcome thereof that ameliorates, palliates, decreases or prevents the symptoms associated with depression; a process or an outcome thereof that improves the symptoms associated with depression; a process or an outcome thereof that normalizes body functions in diseases or disorders that result in impairment of the specific body functions; or a process or an outcome thereof that elicits an improvement in one or more of the clinically measured parameters of the disease. In one embodiment, a treatment objective is to prevent or slow down (i.e. lessen) an undesired physiological condition, disorder or disease, or to obtain a beneficial or desired result. Herein the result can be, e.g., medical, physiological, clinical, physical therapy, occupational therapy, and subjective to a health care worker or to a patient; or can be interpreted in the field as a parameter for "quality of life" or for "activity of daily living". For the purposes of this disclosure, the "beneficial or desired result" can comprise, but are not limited to, alleviation of symptoms; diminution/diminishment of the extent of the condition, disorder or disease; stabilization (i.e., not worsening) of the state of the condition, disorder or disease; delay in onset or slowing of the progression of the condition, disorder or disease; amelioration or palliation of the condition, disorder or disease; and remission (partially or totally), whether detectable or undetectable; or enhancement or improvement of the condition, disorder or disease. In one embodiment, treatment includes eliciting a clinically significant response without excessive levels of side effects. In another embodiment, treatment also includes prolonged survival as compared to expected survival if not receiving treatment. In yet another embodiment, treatment is referred to as the administration of a medicine, or the application of a medical procedure, to a patient. As used herein, treatment can comprise prevention or curing of a weakness or a disease of a patient, or can comprise amelioration of the clinical condition of the patient, including a reduced duration or severity of an illness, an improved quality of life of the patient, or a prolonged survival of the patient.

The term "burst", or "burst firing", as referred to throughout the disclosure, is defined as a firing pattern in neurons that has two or more spontaneous bursts, or spikes of plateau potentials (short as spikes hereafter) in each time of firing (i.e. each burst).

The term "inhibiting burst firing", "inhibition of burst firing", "inhibiting burst", "inhibition of burst", or alike, is referred to as inhibiting a level of neuronal burst firing, which can include: reducing at least one of a number of burst firing cells in the lateral habenula, a ratio of burst firing cells among neurons in the lateral habenula, a probability of the burst firing, a frequency of the burst firing, an amplitude of the burst firing, a duration of the burst firing, or a spike number per burst.

The term "tonic firing" is referred to as a neuronal firing pattern with only one spike in each burst.

BRIEF DESCRIPTION OF THE DRAWINGS

FIGS. 1A and 1B: Western blot analysis showing upregulation of Kir4.1 protein in membrane fraction of habenula of cLH (FIG. 1A) and LPS-induced depression rat models (FIG. 1i). Tubulin is used as loading control. FIGS. 1C and 1D: I-V plot and bar graph showing $Ba^{2+}$-sensitive current in cLH rats and their wild type controls at the age of P60-90 (FIG. 1C) and P30 (FIG. 1D). FIGS. 1E and 1F: Age-dependent learned helpless (FIG. 1E) and forced swim (FIG. 1F) phenotypes of cLH rats. Low number of lever press and high immobility time indicate depressive-like phenotype in P90 cLH rats. Data are means±SEM. Numbers in the bars indicate the number of animals used. *$P<0.05$, $P<0.01$, *$P<0.001$, ****$P<0.0001$; n.s., not significant.

FIG. 2A: Immunohistochemistry signals of Kir4.1 envelope neuronal soma as indicated by white arrows. FIG. 2B: The pan-soma Kir4.1 signals remain intact in LHb of Kir4.1-floxed mice injected with AAV2/1-CaMKII-EGFP-Cre, but are eliminated when injected with AAV2/5-GFAP-EGFP-Cre, (GFAP: human astrocyte-specific GFAP promoter, gfaABC1D). FIG. 2C: Immunogold electron microscopy of Kir4.1. Red arrows indicate gold signals surrounding a neuronal soma. FIG. 2D: I-V plots of the Ba2+ sensitive Kir4.1 current recorded in LHb astrocytes and neurons, with representative traces shown in up-left and statistic bar graph of current recorded when cells are held at −120 mV shown in up-right. Data are means±SEM. ****$P<0.0001$; n.s., not significant.

FIGS. 3A and 3B: Kir4.1 co-immunostaining with neuronal marker (NeuN) or astrocytic marker (S100b and GFAP) in LHb (FIG. 3A) or hippocampus (FIG. 3B). Bottom two panels are staining with the same kir4.1 antibody pre-incubated with the antigen peptide, demonstrating Kir4.1 antibody.

FIGS. 4A-4K show that extracellular potassium is highly correlated with the activity pattern and tightly control by astrocytic kir4.1. FIGS. 4A-4C: Changes of neuronal RMPs caused by $BaCl_2$ (100 μM) in different neuronal types. FIGS. 4D-4E: Correlation between $BaCl_2$-sensitive membrane potential and tonic firing frequency (FIG. 4D), inner burst firing frequency (FIG. 4E) and burst total spike frequency. FIGS. 4G-4H: Representative trace (FIG. 4G) and bar graph (FIG. 4H) shows $BaCl_2$ effect onto bursting neurons. FIG. 4I: Example of a whole-cell patch recording showing LHb neuron spontaneous activity transformed from tonic- to burst-firing mode when Kout is switched from normal (2.75 mM) to half (1.4 mM). FIGS. 4J and 4K: Lowering Kout to half decreases neuronal RMPs (FIG. 4J) and increases the bursting population in neurons (FIG. 4K). *P<0.05, P<0.01, *P<0.001, compared with the control group; n.s., not significant.

FIGS. 5A-5I show that overexpression of astrocytic kir4.1 increases neuronal bursts in LHb and causes depressive-like phenotypes. FIG. 5A: Schematics of AAV vectors engineered to overexpress a control construct and Kir4.1 under GFAP. FIG. 5B: Illustration of bilateral viral injection of AAV-GFAP-Kir4.1 in mouse LHb (stained with antibody against GFP and Hoechst). FIG. 5C: Experimental paradigm for electrophysiology and behavioral testing. FIGS. 5D-5F: Astrocytic overexpression of Kir4.1 decreases RMPs of both astrocytes (FIG. 5D) and neurons (FIG. 5E) and increases the bursting population in neurons (FIG. 5F). FIG. 5G: Histogram of inter-spike intervals (ISI, ms) distribution. The ISIs of LHb neurons in astrocytic Kir4.1-overexpressed mice exhibited a clear bimodal distribution with an extra sharp and condensed cluster of high frequency events centred around 40 ms, indicating a significant weight increase of burst firings. FIGS. 5H and 5I: Behavioral effects of expressing various viral constructs in LHb in forced swim test (FST) (FIG. 5H) and sucrose preference test (SPT) (FIG. 5I). Data are means±SEM. P<0.01, *P<0.001, ****P<0.0001; n.s., not significant.

FIGS. 6A-6L show that loss of function of Kir4.1 in LHb decreases neuronal bursting and rescues depressive-like phenotypes. FIG. 6A: Schematics of the AAV vector engineered to overexpress shRNA or dominant negative form of Kir4.1. H1, human H1 promoter. CAG: The CMV early enhancer/chicken beta actin promoter. FIG. 6B: Western blot and quantification showing efficient knock-down of Kir4.1 by shRNA in HEK293T cells. FIGS. 6C-6H: Electrophysiological characterization in LHb of AAV-Kir4.1-shRNA and AAV-ctrl-shRNA injected rats. Floating bars for membrane slope conductance calculated from the I/V plots (between −120 and +40 mV). FIG. 6D: Experimental paradigm for behavioral testing of cLH rats infected by virus. FIG. 6E: I-V plots showing a shift of reverse potential from −72 mV to −40 mV in astrocytes infected by AAV-Kir4.1-shRNA. FIGS. 6F and 6G: AAV-Kir4.1-shRNA caused more depolarized RMP in astrocytes (FIG. 6F) and neurons (FIG. 6G) in the viral infected region. FIG. 6H: AAV-Kir4.1-shRNA abolished neuronal bursting. FIGS. 6I-6L: Behavioral effects of expressing various viral constructs in the LHb of cLH rats in forced swim (FIG. 6I), learned helpless (FIGS. 6J and 6K) and sucrose preference (FIG. 6L) tests. *P<0.05, P<0.01, *P<0.001, ****P<0.0001, n.s., not significant.

FIG. 8A: Overexpression of Kir4.in LHb does not affect locomotion activities. FIG. 8B: Overexpression of Kir41-shRNA in LHb does not affect locomotion activities. Data are means±SEM. n.s., not significant.

FIGS. 9A-9C show the nucleotide sequence comparison between human, mouse and rat Kir4.1 mRNAs.

FIG. 9D shows the amino acid sequence comparison between human, mouse and rat Kir4.1 proteins.

FIG. 9E shows the sequence alignment results between the target sequence correspond to each of the shRNA No. 1-6 and the human Kir4.1 mRNA sequence.

DETAILED DESCRIPTION

Figure 1A:
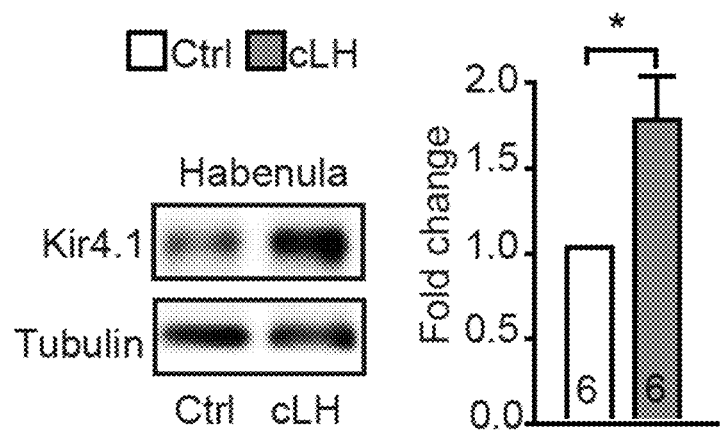
FIGS. 1A-1F show that Kir4.1 is upregulated in the LHb of the animal models of depression.

The nature and benefits of the present disclosure are further described with reference to the following examples, which are intended to illustrate the invention provided herein and not to limit the scope of the present disclosure.

Example 1. Materials and Methods

Animals. Male Wistar rats (12 weeks) and Sprague Dawley rats (3-4 weeks or 12 weeks) were purchased from Shanghai SLAC Laboratory Animal Co. The cLH rats were introduced from Malinow's lab in Cold Spring Harbor of USA, and screened by learned helpless test for breeding as previously described (Schulz et al., 2010). Male cLH rats (3-4 weeks or 12 weeks) were used. Male adult (7-8 weeks of age) C57BL/6 mice (SLAC) were used for virus injection experiments. Animals were group-housed two/cage for rats and four/cage for mice under a 12-h light-dark cycle (light on from 7 a.m. to 7 p.m.). Animals were housed in stable conditions with food and water ad libitum. All animal studies and experimental procedures were approved by the Animal Care and Use Committee of the animal facility at Zhejiang University.

Virus and Plasmid Construct.

For knock-out tests, AAV5-gfaABC1D-GFP-CreMut (titer: $4.74 \times 10^{12}$ v.g./ml) was ordered and prepared by Taitool Bioscience of China. AAV2/1-CamKII-HI-eGFP-Cre were purchase from University of Pennsylvania Vector core, Upenn, USA (Cat #: AV-1-PV2521). All viral vectors were aliquoted and stored at −80° C. until use.

For overexpression of Kir4.1 tests, AAV2/5-gfaABC1D-EGFP-Kir4.1 was prepared, for which pZac2.1 gfaABC1D-eGFP-Kir4.1 plasmid (AddGene, Plasmid #52874) and the AAV virus (Taitool Bioscience of China, titer: $9.19 \times 10^{12}$ v.g./ml) was used. The package and preparation of the Kir4.1 overexpression viral deliver system was ordered and prepared from Taitool Bioscience of China. A blank control, AAV-GFAP::GFP which expressed GFP but not Kir4.1 was also ordered and prepared from Taitool Bioscience of China.

For loss-of-function of Kir4.1 tests, a Kir4.1 mutation construct and viral deliver system (namely AAV5-gfaABC1D-dnKir4.1-2A-eGFP, titer: $4.15 \times 10^{13}$ v.g./ml) wherein GYG at position 130-132 are mutated to be AAA was ordered and prepared from Taitool Bioscience of China.

For another loss-of-function of Kir4.1 test, shRNA constructs and viral deliver systems targeting Kir4.1 were ordered from and prepared by Taitool Bioscience of China.

A total of 6 shRNA sequences were designed by using RNAi designer online software (Invitrogen), which are purported to target the following target sequence in the rat mRNA sequence of rat (as set forth in SEQ ID NO.:7):

1)
5'-GGACGACCTTCATTGACAT-3'; (SEQ ID No. 1)

2)
5'-GCTACAAGCTTCTGCTCTTCT-3'; (SEQ ID No. 2)

3)
5'-GCTCTTCTCGCCAACCTTTAC-3'; (SEQ ID No. 3)

4)
5'-CCGGAACCTTCCTTGCAAA-3'; (SEQ ID No. 4)

5)
5'-GCGTAAGAGTCTCCTCATTGG-3'; (SEQ ID No. 5)
or 6)
5'-GCCCTTAGTGTGCGCATTA-3'. (SEQ ID No. 6)

Six shRNA plasmids were prepared accordingly. In particular, the six shRNA were cloned in a vector named WX231-L (Taitool Bioscience of China, Cat #: WX231) based on the sequences as shown in the following Table 1.

TABLE 1

Sequences for shRNA cloning and construction (each sequence has a direction from 5' end to 3' end).

| shRNA No. | Sticky end | Target seq. | Loop | Rev seq. | PolyT |
|---|---|---|---|---|---|
| shRNA-1 | TCC CC | GGACGACCTT ATTGACAT (SEQ ID No. 1) | TTCA AGAG A | ATGTCAATGA AGGTCGTCC (SEQ ID No. 9) | TTTTT |
|  | TCT AAA AAA | GGACGACCTT ATTGACAT (SEQ ID No. 1) | TCTC TTGA A | ATGTCAATGA AGGTCGTCC (SEQ ID No. 9) | G |
| shRNA-2 | TCC CC | GCTACAAGCTT CTGCTCTTCT (SEQ ID No. 2) | TTCA AGAG A | AGAAGAGCAG AAGCTTGTAG C (SEQ ID No. 10) | TTTTT |
|  | TCT AAA AAA | GCTACAAGCTT CTGCTCTTCT (SEQ ID No. 2) | TCTC TTGA A | AGAAGAGCAG AAGCTTGTAG C (SEQ ID No. 10) | G |
| shRNA-3 | TCC CC | GCTCTTCTCGC CAACCTTTAC (SEQ ID No. 3) | TTCA AGAG A | GTAAAGGTTG GCGAGAAGAG C (SEQ ID No. 11) | TTTTT |
|  | TCT AAA AAA | GCTCTTCTCGC CAACCTTTAC (SEQ ID No. 3) | TCTC TTGA A | GTAAAGGTTG GCGAGAAGAG C (SEQ ID No. 11) | G |
| shRNA-4 | TCC CC | GCCGGAACCTT CCTTGCAAA (SEQ ID No. 19)[1] | TTCA AGAG A | TTTGCAAGGA AGGTTCCGGC (SEQ ID No. 20)[2] | TTTTT |
|  | TCT AAA AAA | GCCGGAACCTT CCTTGCAAA (SEQ ID No. 19)[1] | TCTC TTGA A | TTTGCAAGGA AGGTTCCGGC (SEQ ID No. 20)[2] | G |
| shRNA-5 | TCC CC | GCGTAAGAGTC TCCTCATTGG (SEQ ID No. 5) | TTCA AGAG A | CCAATGAGGA GACTCTTACG C (SEQ ID No. 13) | TTTTT |
|  | TCT AAA AAA | GCGTAAGAGTC TCCTCATTGG (SEQ ID No. 5) | TCTC TTGA A | CCAATGAGGA GACTCTTACG C (SEQ ID No. 13) | G |
| shRNA-6 | TCC CC | GCCCTTAGTGT GCGCATTA (SEQ ID No. 6) | TTCA AGAG A | TAATGCGCAC ACTAAGGGC (SEQ ID No. 14) | TTTTT |
|  | TCT AAA AAA | GCCCTTAGTGT GCGCATTA (SEQ ID No. 6) | TCTC TTGA A | TAATGCGCAC ACTAAGGGC (SEQ ID No. 14) | G |

Note:
[1] The sequence as set forth in SEQ ID No. 19 is substantially the sequence as set forth in SEQ ID No. 4 plus an additional "G" at its 5' end, in order to increase the cloning and/or transcription efficiency;
[2] The sequence as set forth in SEQ ID No. 20 is the reverse complimentary of the sequence as set forth in SEQ ID No. 19, and the sequence as set forth in SEQ ID No. 20 consists substantially of a sequence (TTTGCAAGGAAGGTTCCGG, as set forth in SEQ ID No. 12), which is substantially the reverse complimentary of the sequence as set forth in SEQ ID No. 4, plus a "C" at its 3' end. Such a design is purported to increase the cloning and/or transcription efficiency.

The knocking down efficiency was tested by Western blot of Kir4.1 from HEK293TN cells which were co-transfected with Flag-tagged-Kir4.1 plasmid (pAAV-CMV-betaGlobin-Kir4.1-eGFP-3Flag) and each of the six shRNA plasmids. The fifth sequence, 5'-GCGTAAGAGTCTCCTCATTGG-3', was chosen for use in Kir4.1-shRNA virus package.

AAV5-H1-Kir4.1-shRNA-CAG-eGFP (titer: 3.04×10$^{13}$ v.g./ml) and AAV5-H1-Luciferase-shRNA-CAG-eGFP (titer: 1.46×10$^{13}$ v.g./ml) were ordered and prepared by Taitool Bioscience of China.

LPS-induced depression model. The LPS-induced depression model was conducted as previously described (Adzic et al., 2015). Adult (3 months) Wistar male rats were used for the experiments. LPS (Sigma, L-2880) dissolved in sterile 0.9% saline was intraperitoneally injected into Wistar rats, at a dosage of 0.5 mg/kg. This dosage was used to stimulate a subclinical infection without inducing obvious inflammation and other apparent impairment in the animals. Saline or LPS was injected between 09:30 and 10:30 a.m. daily for 7 days. The forced swim test was performed 24 hours after the last injection. The habenular tissue was dissected 24 hours after the behavioral test.

Stereotaxic surgery and virus injection. cLH rats or mice (postnatal 50-60 days) were deeply anesthetized by using 4% pentobarbital and placed in a stereotactic frame (RWD Instruments, China). All measurements were made relative to bregma for virus/implant surgeries (For rats, LHb: AP, −3.7 mm from bregma; ML, ±0.7 mm; DV, −4.1 mm from the brain surface; for mice: AP, −1.72 mm from bregma; ML, ±0.46 mm; DV, −2.62 mm from the brain surface). Virus injection was performed using a mircoinjection needle with a pressure microinjector (Picospritzer III, Parker, USA) delivering virus at a slow rate of 0.1 ul/min. After the injection was completed, two minutes were allowed to pass and leaving it for an additional 10 minutes before the needle was then slowly withdrawn completely. After surgery, mice recovered from anesthesia under a heat pad.

At least 14 days after injection, mice or rats were used in behavioral or electrophysiological studies. All the injection sites will be checked by immunostaining after the behavioral experiments. Only mice with correct injection site will be counted into the behavioral statistics.

Immunohistochemistry. Animals were anesthetized using 10% chloral hydrate, and then perfused transcardially with ice-cold PBS (pH 7.4) followed by 4% paraformaldehyde. After overnight post fix in 4% paraformaldehyde solution, brains were cryoprotected in 30% sucrose for 1 day (for mice) or 3 days (for rats). Coronal sections (40 μm) were cut on a microtome (Leica) and collected in PBS and stored at 4° C. for further using. The antibodies used were rabbit anti-Kir4.1 extracellular peptide (1:200, Alomone labs), mouse anti-GFAP (1:500, Sigma), mouse anti-NeuN (1:500, Millipore), mouse anti-S100b (1:500, Sigma), chicken anti-GFP (1:1000, Abcam), Alexa Fluor488 goat anti-rabbit IgG, Alexa Fluor488 goat anti-chicken IgG, Alexa Fluor594 goat anti-mouse IgG (all 1:1000, Invitrogen). Specifically, for Kir4.1 staining, the rabbit anti-Kir4.1 extracellular peptide antibody was incubated for 48-72 h and the other primary antibodies were incubated for 36-48 h. For the antibody absorption experiments, the rabbit anti-Kir4.1 extracellular peptide antibody was pre-adsorbed with the Kir4.1 antigen by mixing at the weight ratio of 1:2 for 24 h. Slices were counterstained with Hoechst in the final incubation step to check the injection site. Fluorescent image acquisition was performed with an Olympus Fluoview FV1000 confocal microscope and a Nikon A1 confocal microscope.

Western Blot. The habenular membrane fraction and whole protein was extracted as previously described[11]. Animals were anesthetized using 10% chloral hydrate, and habenular tissue was quickly dissected from the brain and homogenized in lysis buffer (320 mM sucrose, 4 mM HEPES pH7.4, 1 mM $MgCl_2$ and 0.5 mM $CaCl_2$, 5 mM NaF, 1 mM $Na_3VO_4$, EDTA-free, Protease Inhibitor cocktail tablets (Roche)) on ice. The lysis buffer used for extracting the total protein of HEK293TN cell contained 50 mM Tris (pH 7.4), 150 mM NaCl, 1% Triton X-100, 1% sodium deoxycholate, 0.1% SDS and Protease Inhibitor cocktail tablets (Roche). After protein concentration measurement by BCA assay, 10-20 g proteins for each lane was separated on a 10% SDS-PAGE gel and transferred for western blot analysis. Anti-Kir4.1 (1:1000, Alomone labs), anti-GFAP (1:1000, Sigma) and anti-tubulin (1:5000, Bio-Rad) antibodies were used. High sensitive ECL reagent was used (GE Healthcare). All the bands were analyzed with Quantity one or Image J.

LHb brain slice preparation. Rats (P25-30 or P60-90) and mice (P90) were anesthetized with isoflurane and 10% chloral hydrate, and then perfused with 20 ml ice-cold ACSF (oxygenated with 95% $O_2$+5% $CO_2$) containing (mM): 125 NaCl, 2.5 KCl, 25 $NaHCO_3$, 1.25 $NaH_2PO_4$, 1 $MgCl_2$, 2.5 $CaCl_2$) and 25 Glucose, with 1 mM pyruvate added. The brain was removed as quickly as possible after decapitation and put into chilled and oxygenated ACSF. Coronal slices containing habenular (350 μm- and 300 μm-thickness for rats and mice, respectively) were sectioned in cold ACSF by a Leica2000 vibratome and then transferred to ASCF at 32° C. for incubation and recovery. ACSF was continuously gassed with 95% $O_2$ and 5% $CO_2$. Slices were allowed to recover for at least 1 hour before recording.

In vitro electrophysiological recording. For LHb neuron recordings, currents were measured under whole-cell patch clamp using pipettes with a typical resistance of 4-6 MΩ filled with internal solution containing (mM) 105 K-Gluconate, 30 KCl, 4 Mg-ATP, 0.3 Na-GTP, 0.3 EGTA, 10 HEPES and 10 Na-phosphocreatine, with pH set to 7.35. The external ACSF solution contained (in mM) 125 NaCl, 2.5 KCl, 25 $NaHCO_3$, 1.25 $NaH_2PO_4$, 1 $MgCl_2$, 2.5 $CaCl_2$ and 25 Glucose. Cells were visualized with infrared optics on an upright microscope (BX51WI, Olympus). A Multi-Clamp 700B amplifier and pCLAMP10 software were used for electrophysiology (Axon Instruments). The series resistance and capacitance was compensated automatically after stable Giga seal were formed. The spontaneous neuronal activity was recorded under current-clamp (I=0 pA) for consecutive 60 s. RMP was determined during the silent period of the neuronal spontaneous activity.

To test TTX (1 μM, Sigma) and $BaCl_2$ (100 μM, Sigma) effect onto neuronal RMP, baselines of RMP were recorded for at least for 3 min. Drug were then perfused, the arriving of the drug was precisely indicated with a bubble that pre-added before the transition from normal ACSF to drug added ACSF. TTX acts on LHb neuron as quickly as several minutes while $BaCl_2$ takes more 10 min to affect neuronal RMP. The drug effect of TTX and $BaCl_2$ onto neuronal RMP at the time point of 5 min and 15 min were then tested respectively.

Astrocytic patch and Kir4.1 current isolation. Astrocytes were distinguished from neuron by their small (5-10 μm) oval shaped somata and by electrophysiological features: a hyperpolarized RMP and a low input resistance, a linear I-V relationship and an absence of action potentials in response to increased injection currents. $BaCl_2$ (100 μM, Sigma) were applied to isolate Kir4.1 current which is subtracted from the IV curve recorded from −120 mV to 0 mV.

Learned helpless test (LHT). Male juvenile (P30) or adult (P90) cLH rats were tested in a lever-pressing task to evaluate the learned helpless (LH) phenotype[11]. A cue-light-illuminated lever in the shock chamber was presented, which can terminate the shock when rats pressed the lever. 15 escapable shocks (0.8 mA) were delivered with a 24 s inter-shock interval were given. Each shock lasted up to 60 s unless the rat pressed the lever to terminate the shock. Out of the 15 trials, rats which failed to press the lever for more than 10 trials were defined as "learned helplessness" (LH), and rats with less than 5 failures were defined as "non-learned helplessness" (NLH).

Forced swim test (FST). Animals were individually placed in a cylinder (12 cm diameter, 25 cm height for mice; 20 cm diameter, 50 cm height for rats) of water (23-25° C.) and swam for 6 min under normal light. Water depth was set to prevent animals from touching the bottom by tails and hind limbs. Animal behaviors were videotaped from the side. The immobility time during the last 4 min test was counted offline by an observer blind of the animal treatments. Immobility was defined as time when animals remained floating or motionless with only movements necessary for keeping balance in the water. For rats, an additional pre-test was conducted 24 h before the test, during which rats were individually placed in a cylinder of water with conditions described above for 15 min.

Sucrose preference test (SPT). Animals were single housed and habituated with two bottles of water for 2 days, followed by two bottles of 2% sucrose for 2 days. Animals were then water deprived for 24 h and then exposed to one bottle of 2% sucrose and one bottle of water for 2 h in the dark phase. Bottle positions were switched after 1 h. Total consumption of each fluid was measured and sucrose preference was defined as the ratio of sucrose consumption divided by total consumptions of water and sucrose.

Statistical analyses. Required sample sizes were estimated based on our past experience performing similar experiments. Animals were randomly assigned to treatment groups. Analyses were performed in a manner blinded to treatment assignments in all behavioral experiments. Statistical analyses were performed using GraphPad Prism software v6. By pre-established criteria, values were excluded from the analyses if the viral injection or drug delivering sites were out of LHb. All statistical tests were two-tailed, and significance was assigned at P<0.05. Normality and equal variances between group samples were assessed using the D'Agostino & Pearson omnibus normality test and Brown-Forsythe tests respectively. When normality and equal variance between sample groups was achieved, one-way ANOVAs (followed by Bonferroni's multiple comparisons test), or t test were used. Where normality or equal variance of samples failed, Mann-Whitney U test were performed. Linear regression test, Chi-square test was used in appropriate situations.

Example 2. Kir4.1 is Upregulated in LHb of Animal Models of Depression

Figure 1B:
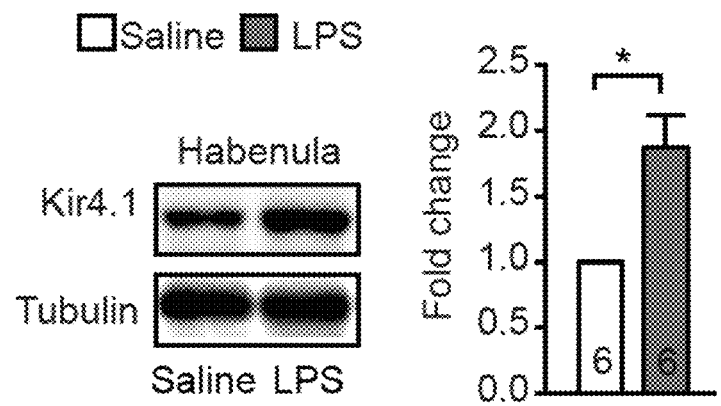

Western blot analysis confirmed that Kir4.1 had a significant increase (1.75-fold) in the membrane protein extraction of cLH habenulae (FIG. 1A). To test whether Kir4.1 upregulation is universal in depression, an additional depression animal model, the LPS (lipopolysaccharide)-induced depression was used. One week of LPS injection (0.5 mg/kg, i.p.) in 3-month-old Wistar rats was sufficient to cause strong depressive-like phenotype in the forced swim test (FST). The Kir4.1 level was also significantly increased in the LPS-depression rats (FIG. 1B, 1.87-fold).

Figure 1C:
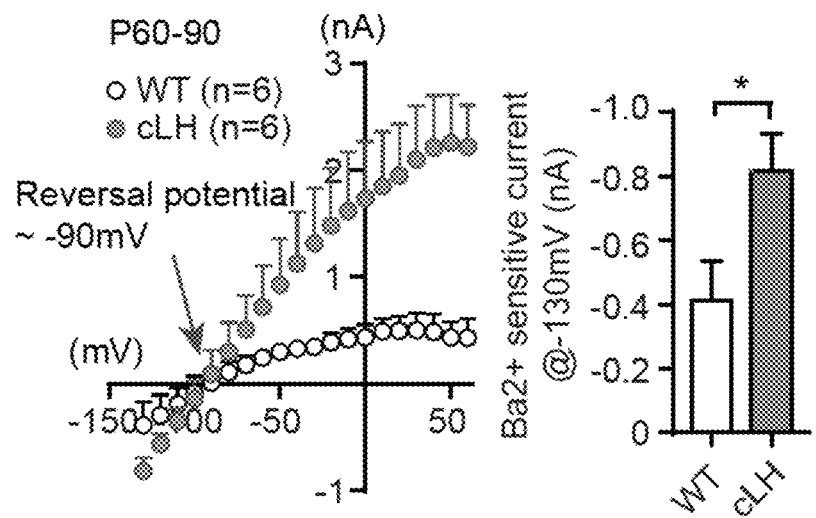
Figure 1D:
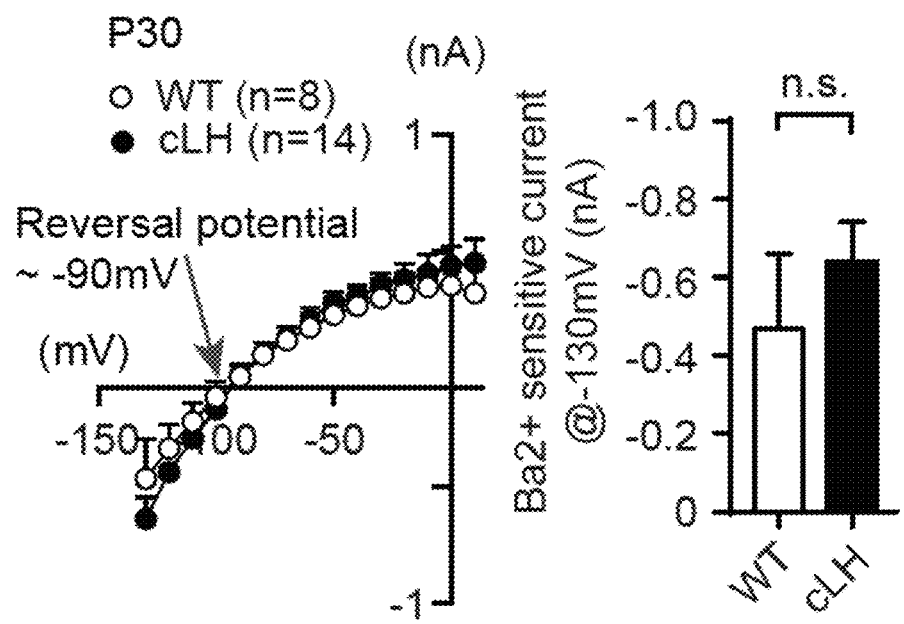
Figure 1E:
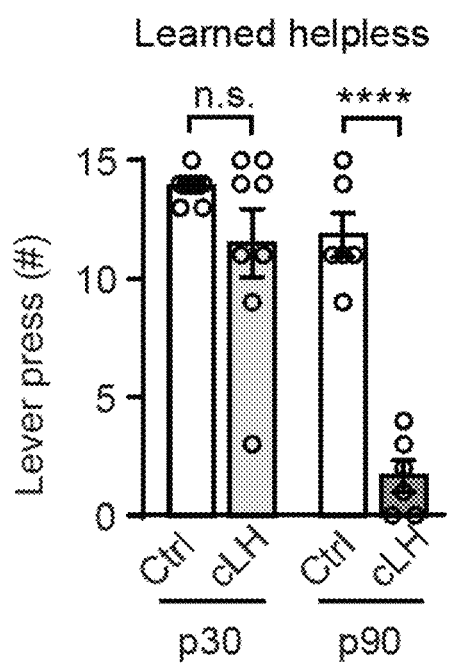
Figure 1F:
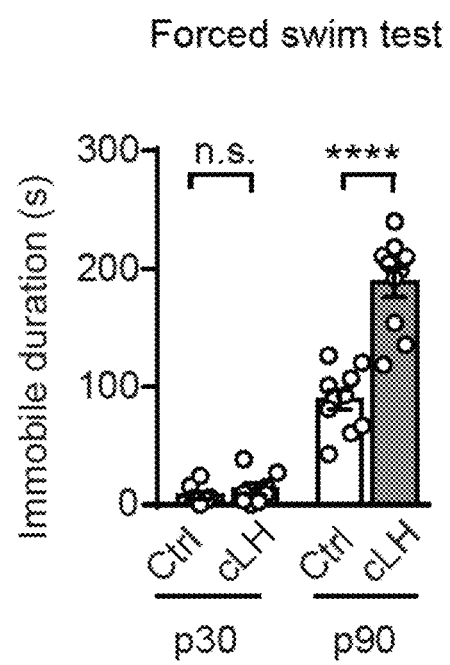

Kir4.1 is a principal component of the glial Kir channel and is largely responsible for mediating the K+ conductance and setting the RMP of astrocytes. To confirm that Kir4.1 function is indeed upregulated, whole-cell patch clamp was performed onto the astrocytes in brain slices made from the LHb of cLH or SD rats. Astrocytes were distinguished from neurons by their small (5-10 µM) oval shaped somata and electrophysiological features including a relatively hyperpolarized RMP (−74±1 mV), a low input resistance Rin (47±6 MΩ), a linear I-V relationship and an absence of action potentials in response to depolarizing current injections (FIG. 1C). $Ba^{2+}$ ($BaCl_2$, 100 µM) was then bath applied, which selectively blocks Kir channels at sub-mM concentrations, to isolate Kir4.1 current. The $Ba^{2+}$-sensitive currents displayed a reversal potential close to Ek (−90 mV) (FIGS. 1E and 1F), indicating it represents the K+ conductance. It was found that $Ba^{2+}$-sensitive currents in LHb astrocytes were almost doubled in cLH rats, compared with SD controls, at the age of P60-90 (FIG. 1C). Interestingly, the increase of Kir4.1 current was not obvious at P30 (FIG. 1D). At this age, cLH rats did not yet show depressive-like phenotypes in both learned helpless test (LHT, FIG. 1E) and the forced swim test (FST, FIG. 1F), suggesting that level of Kir4.1 overexpression correlated with the developmental onset of the depressive-like symptoms.

Figure 2A:
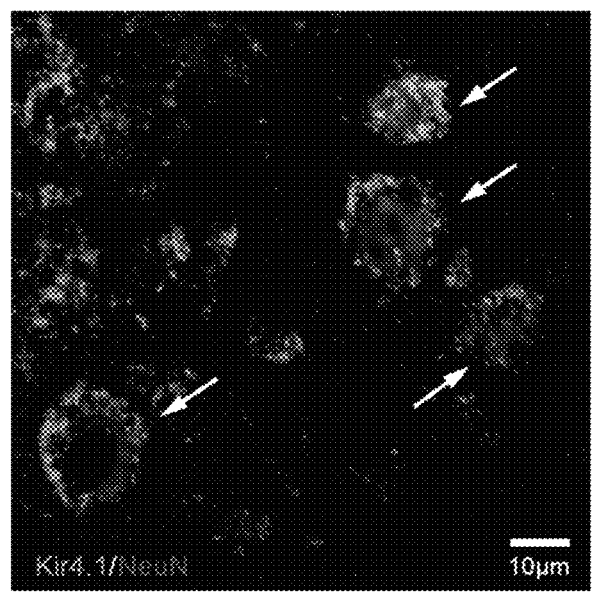
FIGS. 2A-2D show that Kir4.1 is expressed on astrocytic processes tightly wrapping around neuronal soma.
Figure 2B:
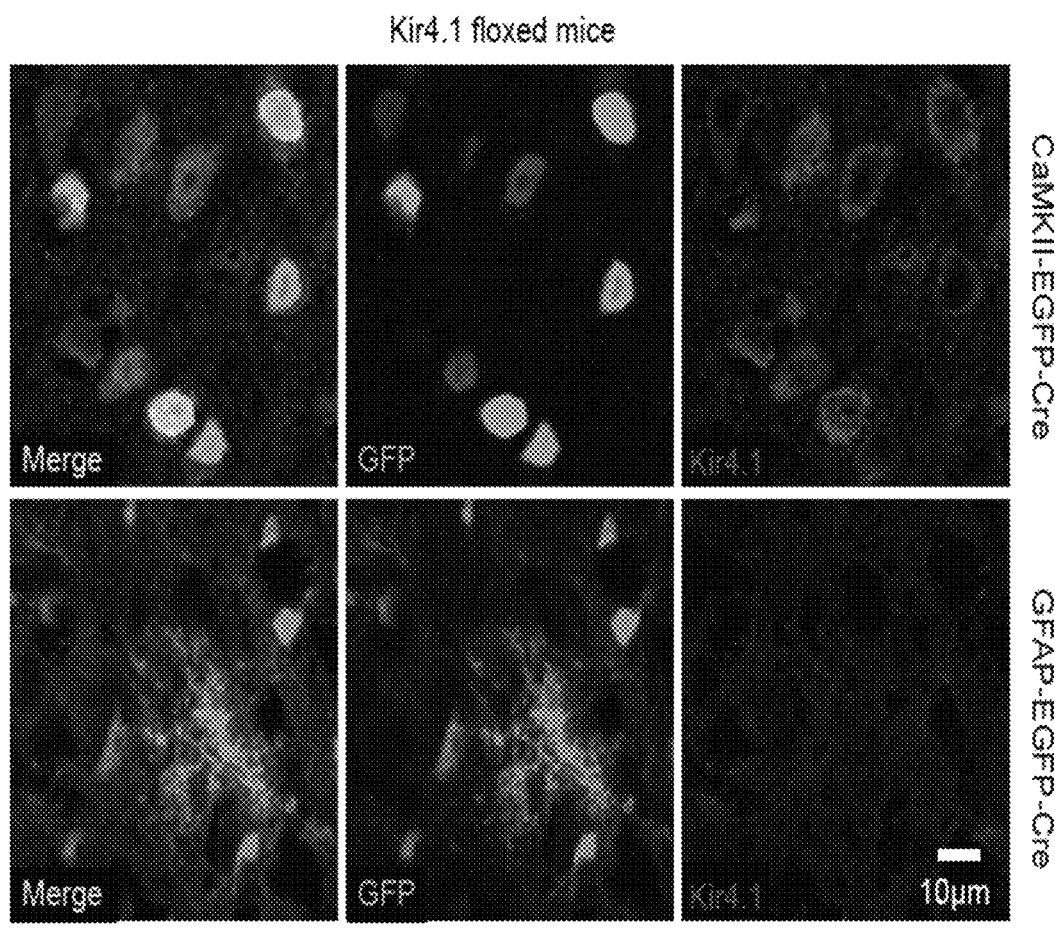
Figure 2C:
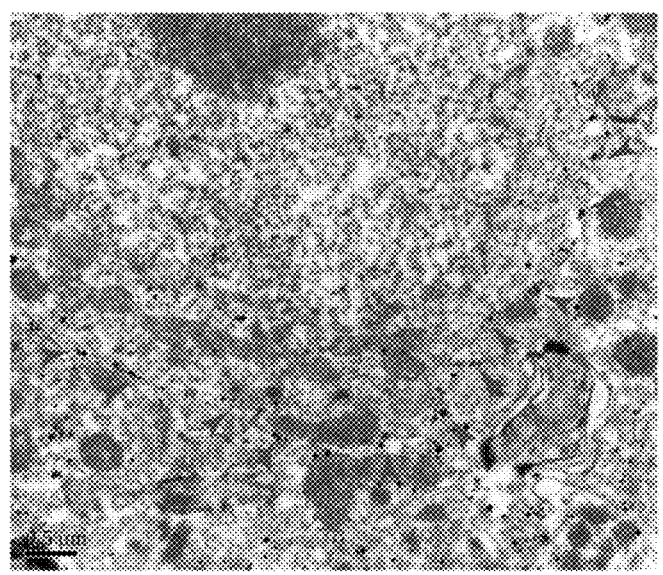
Figure 2D:
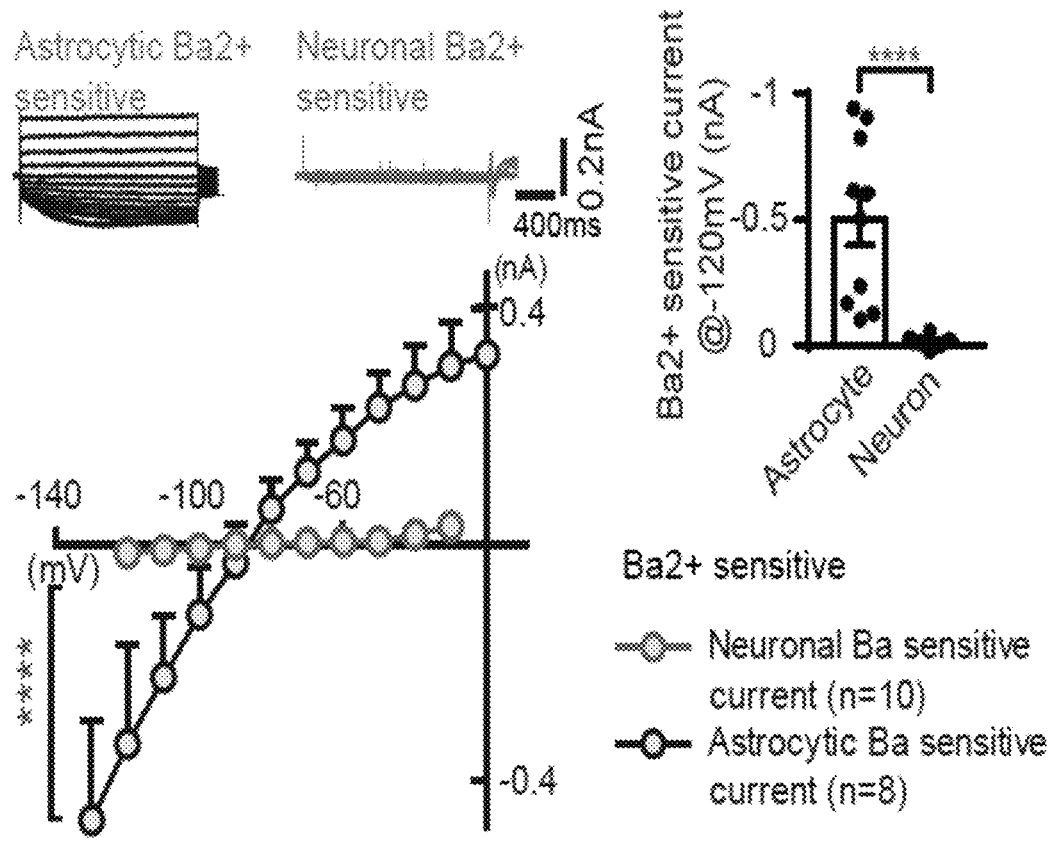
Figures 3A, 3B:
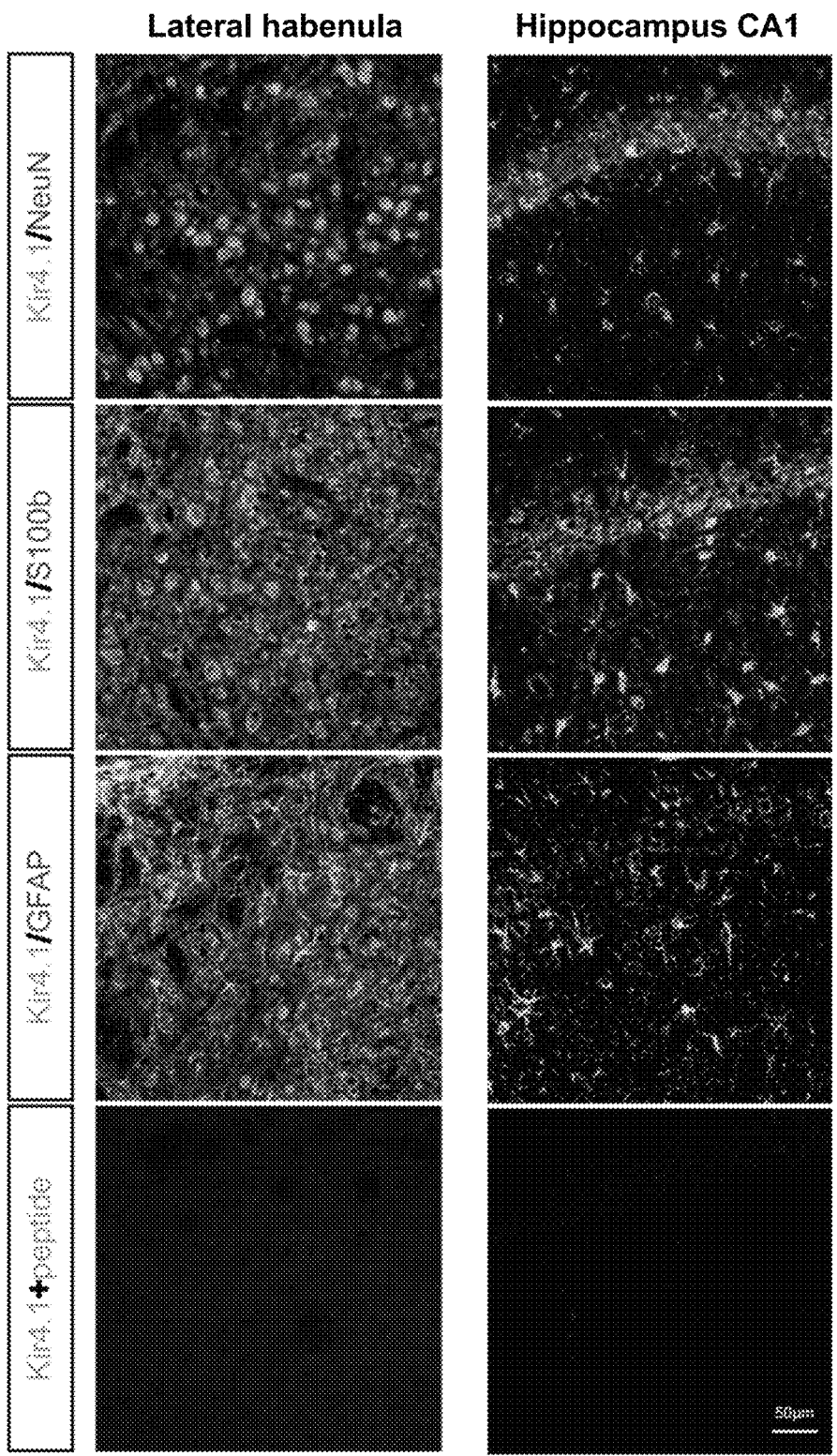
FIGS. 3A-3B show that Kir4.1 is expressed in astrocytic processes of LHb and astrocytic soma of hippocampus.

Example 3. Kir4.1 are Expressed on Astrocytic Processes Tightly Wrapping Around Neuronal Soma As an inwardly rectifying $K^+$ channel, Kir4.1 has been strongly implicated in buffering excess extracellular $K^+$ in tripartite synapses. Conventional model of $K^+$ buffering suggests Kir4.1 to be highly expressed in astrocytic endfeet surrounding synapses. Surprisingly, with immunohistochemistry co-labeling, Kir4.1 staining in LHb appeared to overlap with the neuronal marker NeuN at low magnification (20x, FIG. 3A), although in the same brain slice Kir4.1 staining patterns in hippocampus were typical astrocytic-looking (FIG. 3B). However, higher magnification imaging with single layer scanning (0.76 µm per layer) revealed that Kir4.1 staining enveloped NeuN signals (FIG. 2A). To confirm that Kir4.1 indeed locates within astrocytes but not neurons in LHb, kir4.1 was separately knocked out in either neurons or astrocytes by injecting AAV virus expressing the cre recombinase under either the neuronal promoter CaMKII or glial promoter GFAP (gfaABC1D) into Kir4.1-floxed mice by using AAV5-gfaABC1D-GFP-CreMut (titer: 4.74× $10^{12}$ v.g./ml), which was provided as mentioned in Example 1. The neural-surrounding staining of Kir4.1 remained intact with neuronal knock-out, but was completely eliminated with astrocytic knock-out (FIG. 2B). Electron microscopy imaging revealed that Kir4.1-positive gold particles were distributed encircling the membrane of neuronal cell bodies (FIG. 2C), as well as in the synapses. Consistently, whole-cell-patch recordings showed that $Ba^{2+}$-sensitive currents are absent in neurons but abundant in astrocytes in LHb (FIG. 2D). Together these results suggest that Kir4.1 is mainly expressed in astrocytic processes tightly wrapping around neuronal soma and synapses in LHb.

Figure 4A:
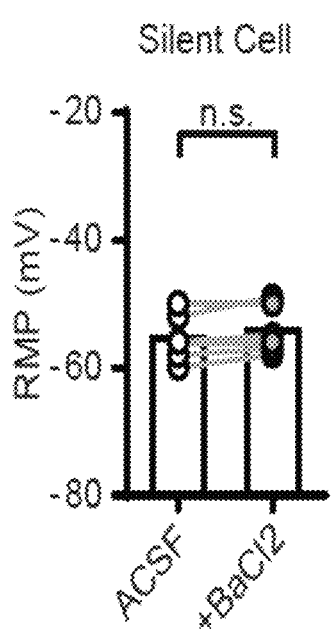
Figure 4B:
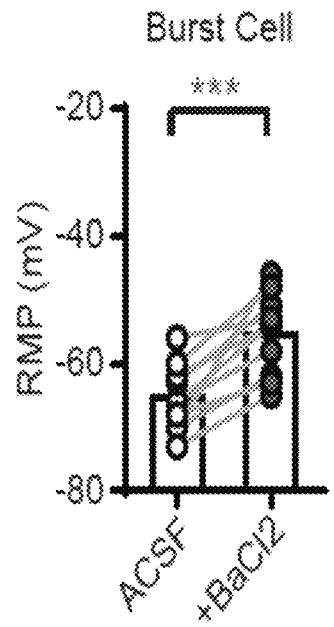
Figure 4C:
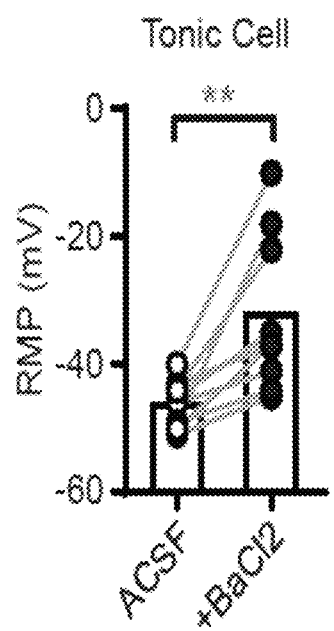
Figure 4D:
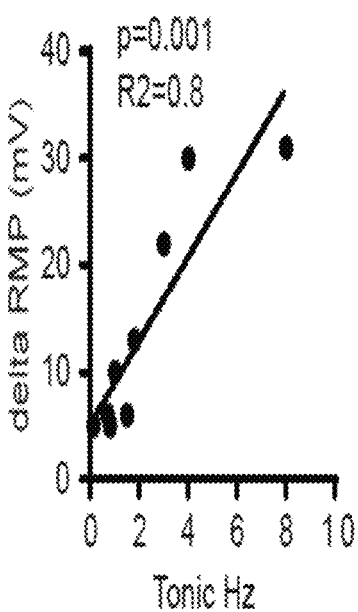
Figure 4E:
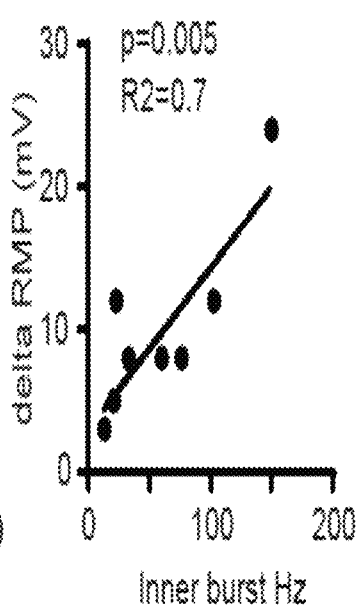
Figure 4F:
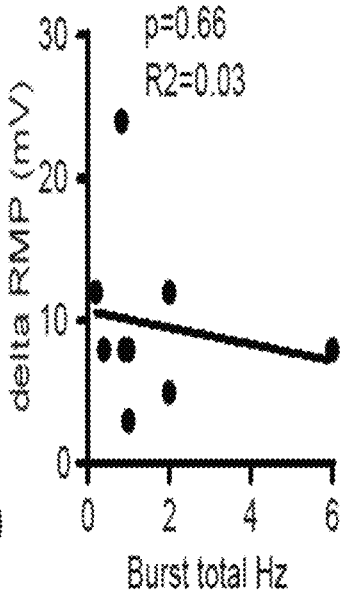

Example 4. Kir4.1-Mediated K Buffering Regulates Neuronal RMP and Bursting Activity How does an astrocytic potassium channel regulate RMP and burst firing of the LHb neuron? The inventors hypothesize that within the highly confined extracellular space between neuronal soma and Kir4.1-positive astrocytic processes (FIGS. 2A-2D), the majority of constantly-released K+ from intrinsically active LHb neurons is quickly cleared by astrocytes through a Kir4.1-dependent mechanism. Accordingly, the Inventors predicted that blockade of Kir4.1 should compromise K+ spatial buffering, resulting in increased extracellular K+ (Kout), and according to Nernst Equation, depolarized neuronal RMPs. Consistent with this prediction, blocking Kir4.1 with $BaCl_2$ depolarized LHb RMPs of tonic and burst-firing, but not silent neurons, after about 10 min bath perfusion of $BaCl_2$ (FIGS. 4A-4C). The amount of changes in RMP positively correlated with the original firing rates of neurons (FIGS. 4D-4F), indicating the more active the neuron is, the larger contribution the K+ buffering to its RMP. Consequent to the RMP change, perfusion of $BaCl_2$ caused a dramatic increase of firing frequency until the neuron reached a sustained plateau of a tetanus response and stopped firing (FIGS. 4G-4H).

Example 5. Enhanced Capacity of Extracellular $K^+$ Clearance Due to Kir4.1 Overexpression May Underlie the Neuronal Hyperpolarization Required for Burst Initiation To assess a causal relationship between Kout and firing mode, current-clamp recordings of LHb neurons were made while lowering Kout from 2.75 mM to 1.4 mM (FIG. 4I). This led to lowered neuronal RMP by 13.7+/−0.5 mV (FIG. 4J) and a direct shift of originally tonic-firing neurons into bursting mode (FIG. 4I). Consequently, percentage of bursting neurons was increased from 8% to 23% (FIG. 4K). In summary, by increasing astrocytic Kir4.1 expression or decreasing the extracellular K+ concentration, it was able to phenocopy in WT animals several key neuronal properties observed in the LHb of animal models of depression, namely hyperpolarized RMPs and enhanced bursts. These results indicate that enhanced capacity of extracellular K⁺ clearance due to Kir4.1 overexpression may underlie the neuronal hyperpolarization required for burst initiation.

Figure 5C:
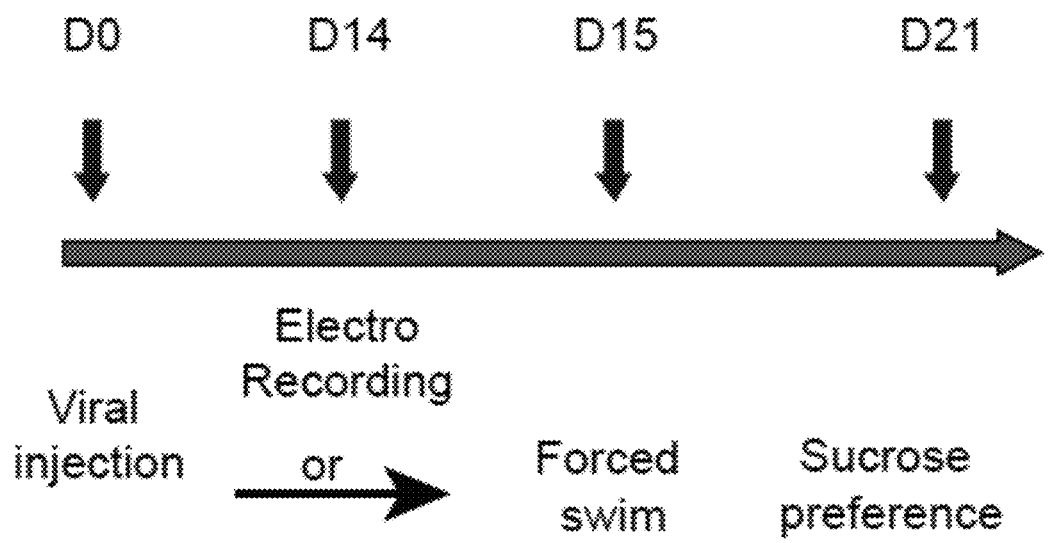

Example 6. Overexpression of Kir4.1 in LHb Astrocytes Increases Neuronal Bursts and Causes Strong Depressive-Like Behaviors To test the effects of Kir4.1 upregulation in LHb, a Kir4.1 overexpression system AAV2/5-gfaABC1D-EGFP-Kir4.1 (namely "AAV-Kir4.1" or "AAV-GFAP::Kir4.1") was prepared and assayed, which uses adeno-associated viruses of the 2/5 serotype (AAV2/5) that preferentially target astrocytes as the vector, together with the human GFAP (gfaABC1D) promoter for the expression. The Kir4.1 overexpression system GFP-tagged Kir4.1 channels (AAV-GFAP::Kir4.1) was prepared as described in Example 1, while AAV-GFAP::GFP which expressed GFP but not Kir4.1 was used as a control (FIG. 5A).

Figures 5D, 5E:
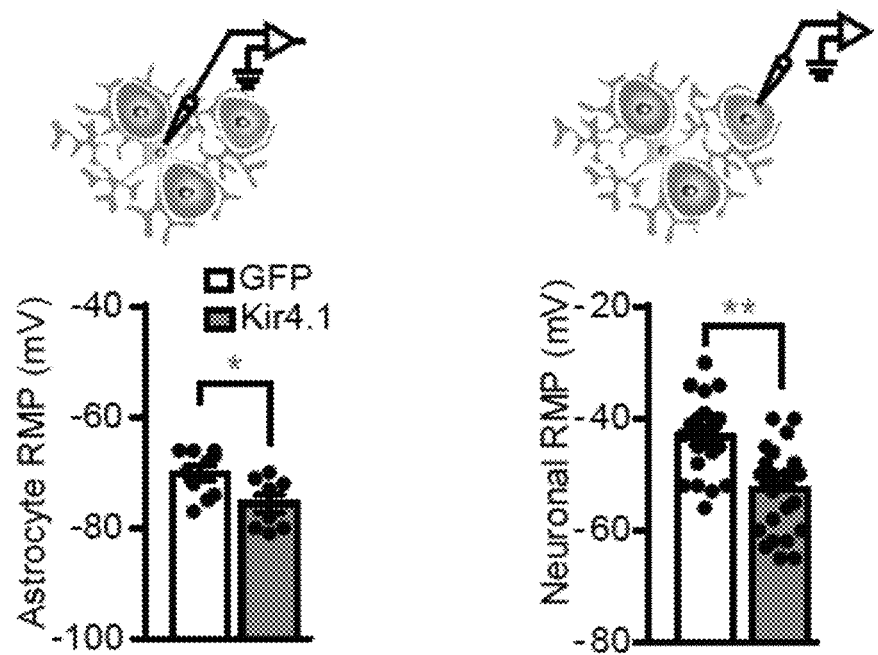
Figure 5F:
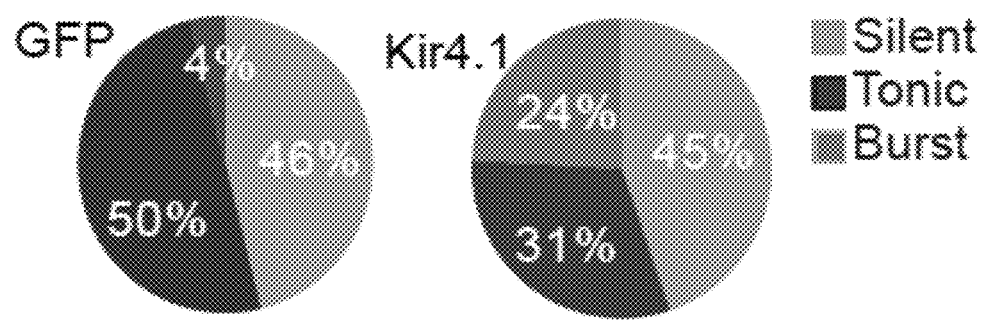
Figure 5G:
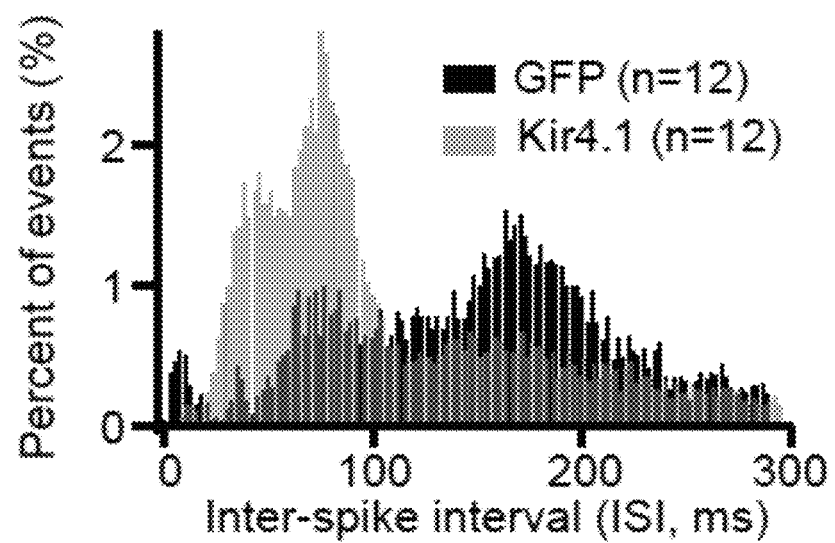

14 days after bilateral injection in the LHb at P50, AAV2/5-mediated viral transduction led to Kir4.1 and GFP expression in astrocytes throughout the LHb (FIG. 5B). Whole-cell recordings were made from either astrocytes or neurons surrounding the viral-transfected astrocytes in coronal LHb slices. The RMPs of both astrocytes and neurons were more hyperpolarized (FIGS. 5D and 5E) and the percentage of bursting neurons were significantly higher (FIG. 5F) in mice infected with AAV-GFAP::Kir4.1 than with AAV-GFAP::GFP.

Figure 5H:
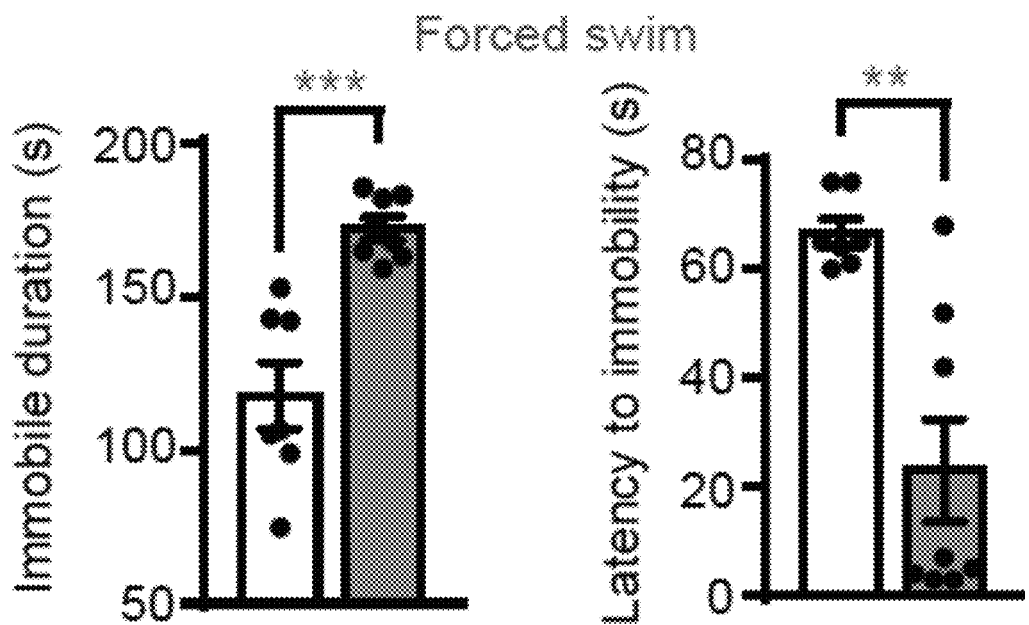
Figure 5I:
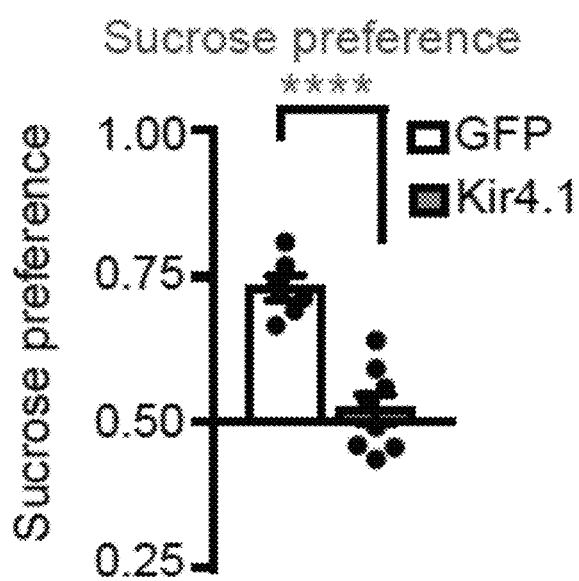

Depressive-like phenotypes were then assayed on and it was found that mice with AAV-GFAP::Kir4.1 infection in the LHb displayed severe depressive-like behaviors (FIGS. 5C-5I), including increased immobile duration and decreased latency to immobility in FST (FIG. 5H), and decreased sucrose preference in the sucrose preference test (SPT, FIG. 5I).

Figure 6A:
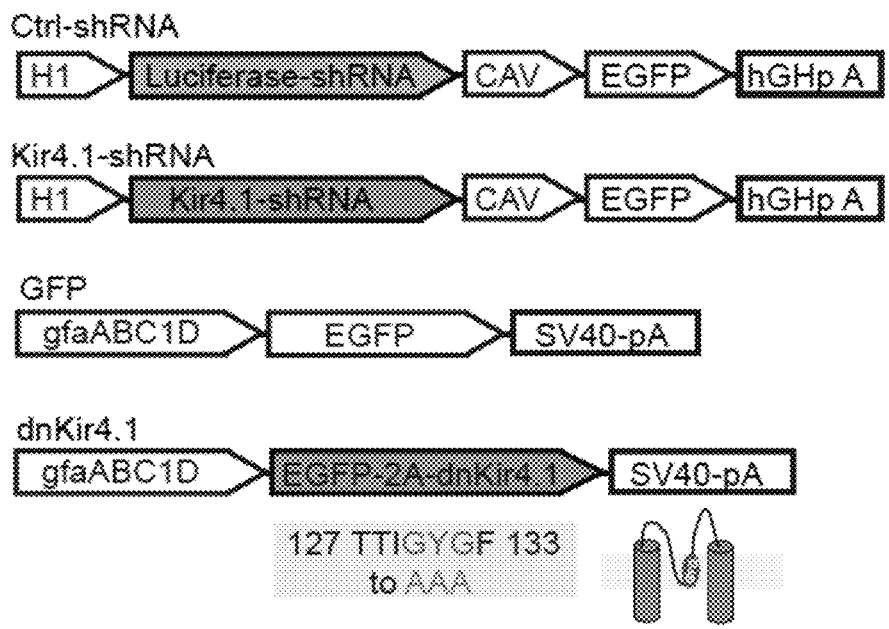

Example 7. Loss-of-Function of Kir4.1 in LHb Decreases Neuronal Bursting and Rescues Depressive-Like Phenotypes Next, to determine whether loss-of-function of Kir4.1 in LHb may reverse depressive phenotypes, two strategies were tried by using AAV2/5 viral vectors to express either a short hairpin RNA (shRNA) to knock down the level of Kir4.1, or a dominant negative construct to block its function in the LHb of cLH rats (FIG. 6A).

Figure 6B:
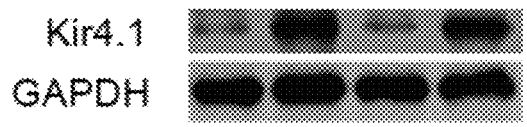
Figure 6B:
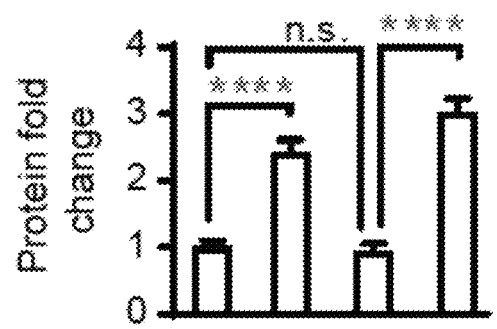
Figure 7:
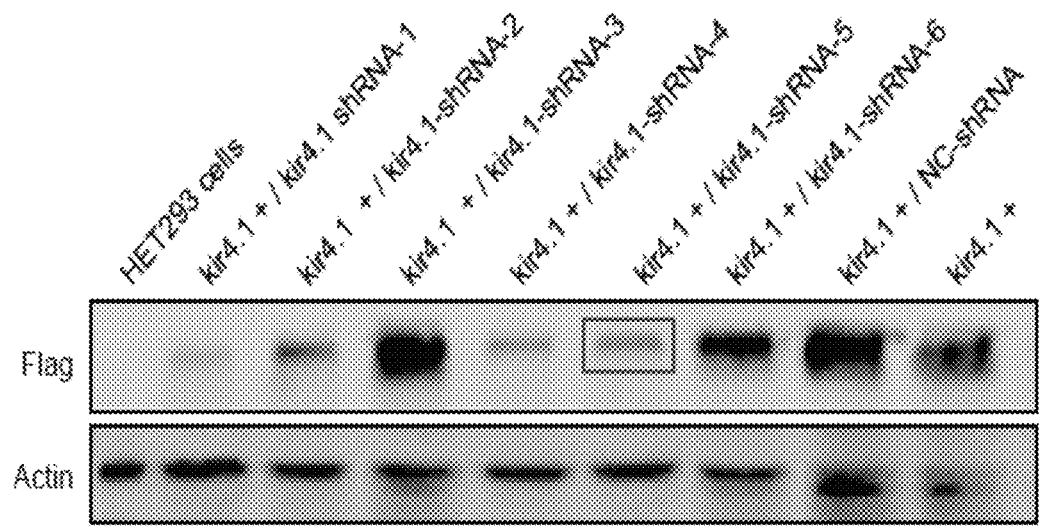
FIG. 7 shows characterization of Kir4.1 loss-of-function constructs. Flag-tagged-Kir4.1 plasmid (pAAV-CMV-beta-Globin-Kir4.1-eGFP-3Flag) was co-transfected with pAAV-vector expressing 6 different shRNAs (see Methods) of Kir4.1 or the negative control (shRNA of luciferase) into HEK293TN cell. Based on the knock-down efficiency as shown in the western blot, Kir4.1-shRNA-5 was chosen for viral package.
Figures 8A, 8B:
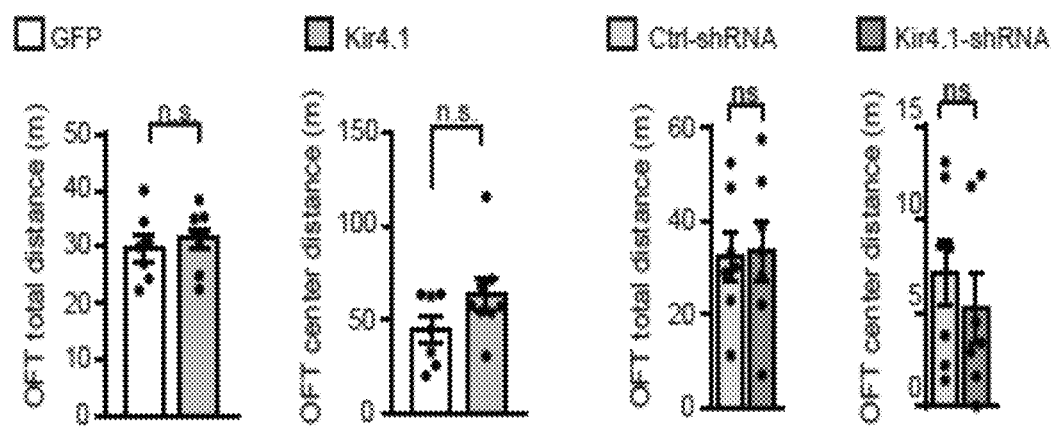
FIGS. 8A-8B show that overexpression of Kir4.1 or Kir4.1-shRNA in LHb does not affect locomotion in open field test.

Six shRNAs specifically targeting the Kir4.1 transcript in cell culture were tested. The results showed that the knock-off efficient of these 6 shRNAs were: Kir4.1-shRNA-1>Kir4.1-shRNA-4/Kir4.1-shRNA-5>Kir4.1-shRNA-2>Kir4.1-shRNA-6>Kir4.1-shRNA-3. The one with most efficient knock-down efficiency was chosen for viral package (FIG. 6B and FIG. 7). After viral expression of this shRNA under the H1 promoter in the LHb of cLH rats (FIG. 6C), its effect was examined on glial and neural electrophysiological properties. In astrocytes infected with the AAV-Kir4.1-shRNA vector, it was found that a dramatic change of I-V relation (FIG. 6E) and a 32 mV depolarization compared with neighboring non-infected astrocytes and 41 mV depolarization compared with ctrl-shRNA-GFP+ astrocytes (FIG. 6F). In neurons infected with the AAV-Kir4.1-shRNA vector, the RMPs did not differ from neighboring non-infected neurons (because neurons do not express Kir4.1 endogenously, FIG. 6G). However, RMPs of LHb neurons from AAV-Kir4.1-shRNA-infected brain slices were overall more depolarized than RMPs of those from AAV-luciferase-shRNA-infected rats (−43±2 mV vs. −53±2.7 Mv, FIG. 6G), suggesting that knock-down of Kir4.1 in astrocytes had a global impact on RMPs of neighboring neurons. Most importantly, bursting activity in LHb of cLH rats were completely eliminated by AAV-Kir4.1-shRNA viral infection (from 29% to 0%, FIG. 6H).

Figures 6J, 6K:
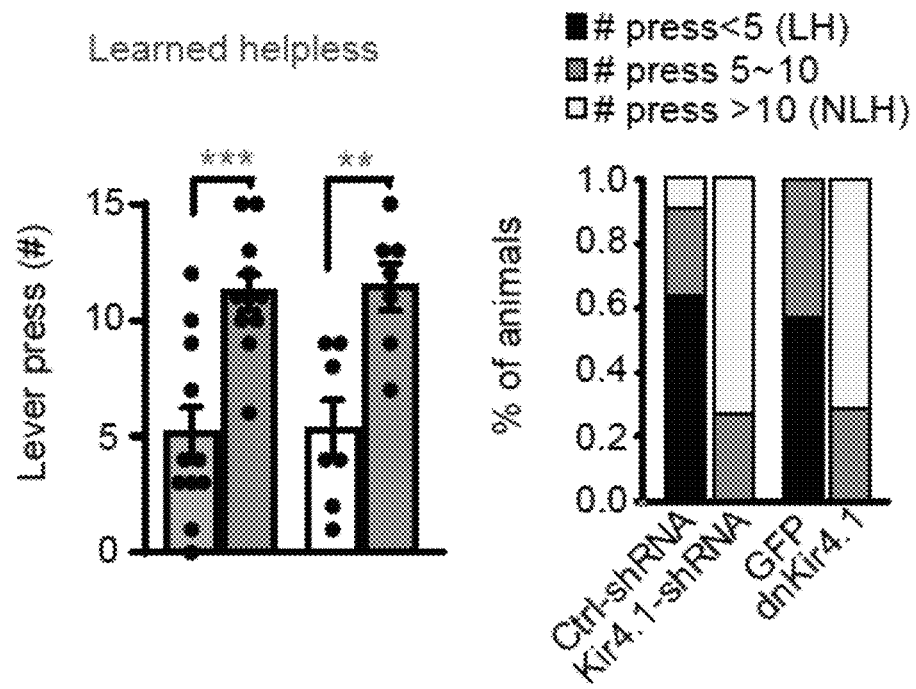
Figure 6L:
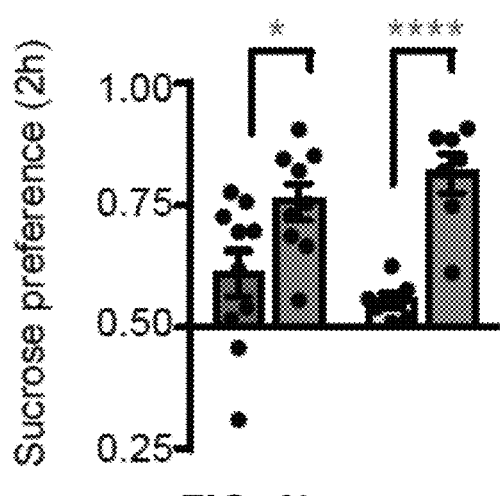

Behaviorally, infection of AAV-Kir4.1-shRNA had a pronounced effect on rescuing the depressive-like phenotypes of cLH rats in three depression paradigms: reducing the immobility time and increasing latency to immobility in FST (FIG. 6I), increasing bar pressing number in the LHT (FIGS. 6J and 6K), and increasing the sucrose preference score in SPT (FIG. 6L).

To avoid an off-target effect of shRNA, a dominant-negative form of Kir4.1, dnKir4.1, containing a GYG to AAA point mutation at the channel pore which blocks K⁺ channels was also tested. The preparation of the Kir4.1 mutation construct and viral deliver system (namely AAV-dnKir4.1, or AAV5-gfaABC1D-dnKir4.1-2A-eGFP) was prepared as described in Example 1. Infection of AAV-dnKir4.1 caused similarly strong anti-depression effects in cLH rats (FIGS. 6I-6L): reducing the immobility time and increasing latency to immobility in FST (FIG. 6I), increasing bar pressing number in the LHT (FIGS. 6J and 6K), and increasing the sucrose preference score in SPT (FIG. 6L).

Example 8. Kir4.1 is Highly Conserved Across the Species from Rat to Human

The experiments as described above, which have largely been performed using rodent animal models (i.e. rat and mouse), have established a crucial role of the inward rectifier potassium (Kir) channel Kir4.1 (or KCNJ10) that is specifically expressed in the astroglial tissues or astrocytes in the lateral habenula (LHb) in causing the depression-like phenotype, at least in these rodent animal models. LHb Kir4.1 has been demonstrated to be able to regulate neuronal resting membrane potential (RMP) and bursting, and importantly, has been shown to be significantly upregulated in depression. The gain-of-function and the loss-of-function manipulations of Kir4.1 in the rodent animals have been shown to respectively cause and rescue depression, indicating that astroglial Kir4.1 is both necessary and sufficient for causing depression. Thus these above results point to Kir4.1 in the LHb as a potential target for treating clinical depression.

In order to estimate whether, and to what extent, the above study results can be translated into other higher species like humans, a series of sequence conservation studies is performed.

Figure 9E:
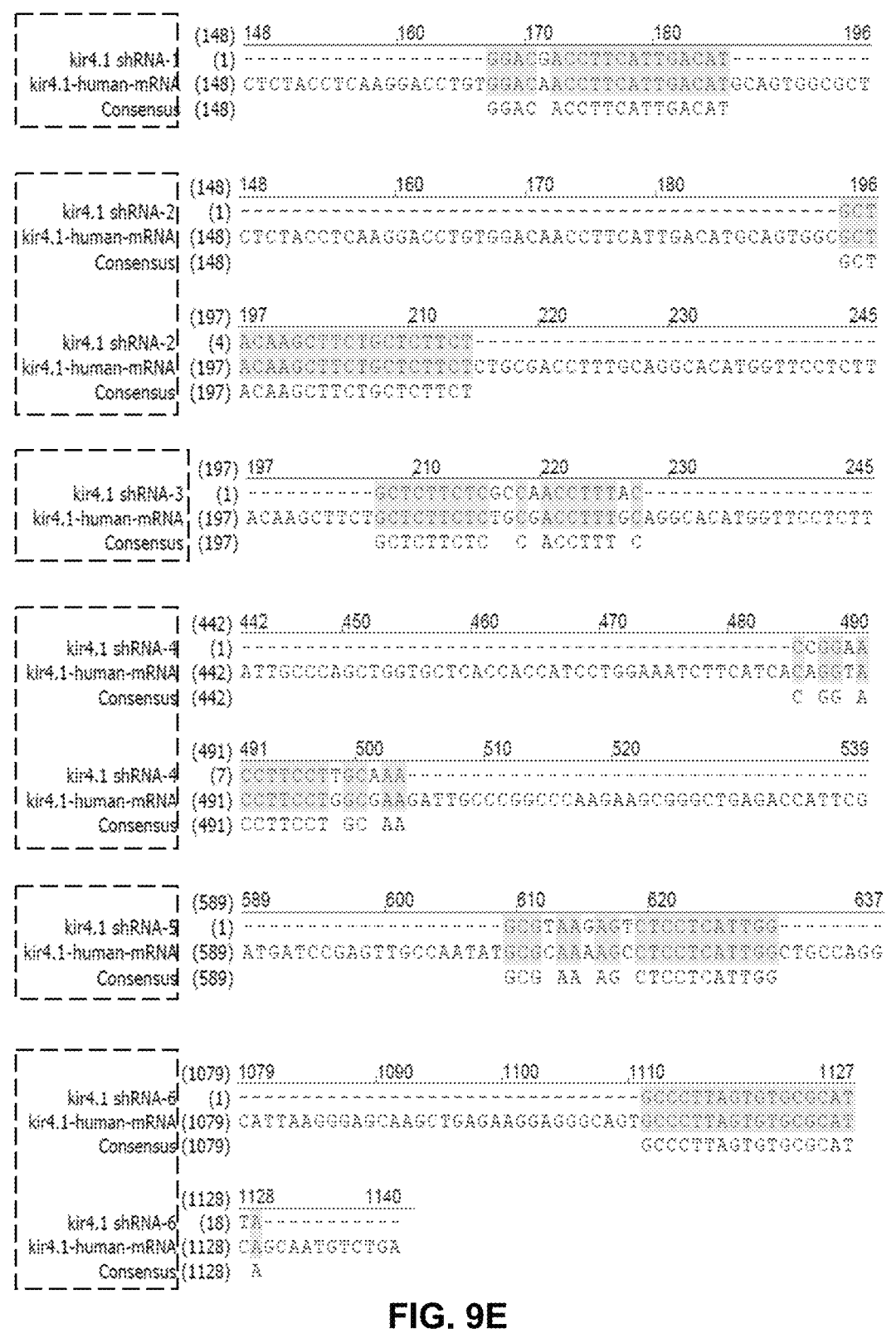

Firstly, a comparative study among the Kir4.1 mRNA sequences of rat (as set forth by SEQ ID NO. 7, see NCBI Reference Sequence: NM_031602.2), mouse (as set forth by SEQ ID NO. 15, see NCBI Reference Sequence: NM_001039484.1), and human (as set forth by SEQ ID NO. 17, see NCBI Reference Sequence: NM_002241.5) has shown that 86.7% of the nucleotide residues are identical, and 98.9% of the nucleotide residues show at least a consensus across the three species (FIGS. 9A-9C).

Secondly, a comparative study among the Kir4.1 amino acid sequences of rat (as set forth by SEQ ID NO. 8, see NCBI Reference Sequence: NP_113790.2, which corresponds to NM_031602.2), mouse (as set forth by SEQ ID NO. 16, see NCBI Reference Sequence: NP_001034573.1, which corresponds to NM_001039484.1), and human (as set forth by SEQ ID NO. 18, see NCBI Reference Sequence: NP_002232.2, which corresponds to NM_002241.5) has shown that 97.9% of the amino acid residues are identical, and 99.7% of the amino acid residues show at least a consensus across the three species (FIG. 9D).

Given the extremely high conservation between human Kir4.1 and rodent Kir4.1 in terms of the mRNA sequences (having 98.9% consensus positions) and the protein sequences (having 99.7% consensus positions), Kir4.1 shall play a similarly crucial role in the lateral habenula (LHb) in the pathogenesis and maintenance of depression.

A survey over the above mentioned Kir4.1-targeting shRNAs (shRNA NOS. 1-6) has shown that each of their corresponding target sequences on the rat Kir4.1 mRNA sequence (i.e. as set forth in SEQ ID NO. 7), which are respectively set forth in SEQ ID NOS. 1-6, also represents a relatively high level of homology in the alignment (see FIG. 9E) with the human mRNA sequence of Kir4.1 (i.e. as set forth in SEQ ID NO. 17), with the 21-base target sequence for shRNA-2 (as set forth in SEQ ID NO. 2) being 100% identical, only one-base difference for both the 19-base target sequences of shRNA-1 and shRNA-6 (as set forth in SEQ ID NOS. 1 and 6 respectively), three-base difference for the 21-base target sequence of shRNA-5 (as set forth in SEQ ID NO. 5), and four-base difference for the 21-base target sequences of shRNA-3 and for the 19-base target sequences of shRNA-4 (as set forth in SEQ ID NOS. 3 and 4, respectively). As such, among the 6 shRNAs that have been utilized for suppressing expression of rat Kir4.1, at least the shRNA-2, likely the shRNA-1, 6 and 5, and potentially shRNA-4 as well, can be utilized to suppress the expression of human Kir4.1, and thus can serve as a component of a pharmaceutical agent capable of inhibiting the activity of the astroglial potassium channel Kir4.1 in a human subject with depression to suppress the bursting activity of neurons in a lateral habenula of the subject for treatment of the disease.

Regarding the dominant negative mutant form of Kir4.1 protein (i.e. dnKir4.1), containing a GYG-to-AAA point mutation corresponding to position 130-132 of the amino acid sequence of wild-type Kir4.1 protein of rat Kir4.1 (as set forth in SEQ ID NO. 8), since the three-amino-acid sequence is strictly conserved within the 88-amino acid context region at positions 101-188 of all of the human, mouse and rat Kir4.1 proteins (as respectively set forth in SEQ ID NOS. 18, 16 and 8, see FIG. 9D), tissue-specific overexpression of such a mutant protein in the LHb of a human subject is expected to also interfere with the normal functionality of Kir4.1 in a dominant negative manner, and consequently, the bursting activity in the LHb of the human subject can be eliminated, thereby realizing an effective treatment of depression in the human subject. As such, the dnKir4.1 can similarly be used as a pharmaceutical agent capable of inhibiting the activity of the astroglial potassium channel Kir4.1 in a human subject with depression to suppress the bursting activity of neurons in a lateral habenula of the subject for treatment of the disease.

Notably also, the vectors that have been utilized for the astrocyte-specific expression of shRNAs or dnKir4.1 in the rat studies as described above, such as AAV-GFAP, and esp. the AAV2/5 shall also be able to realize a similar astrocyte-specific expression of shRNAs (e.g. shRNA-2) and dnKir4.1 to be able to exert the therapeutic effects.

The present disclosure for the first time and unexpectedly find that burst in neurons of the lateral habenula has an important role in the cause of depression, and identify key factors affecting the burst in the lateral habenula, including that the activation of NMDA receptors is the sufficient and necessary condition for inducing burst in the lateral habenula, and that burst in the lateral habenula need the participation of neuron membrane hyperpolarization and T-type low voltage activate calcium channel. Particularly, the present disclosure for the first time and unexpectedly find that it is the burst instead of whole neuron firing or neuron discharges that contribute to the cause of depression. The inventors provide a method and medicament for diagnosing and treating (inhibiting) depression by inhibiting burst in lateral habenula, especially method and medicament for rapidly treating (inhibiting) depression.

Unless otherwise indicated, the practice of the present disclosure will employ common technologies of organic chemistry, polymer chemistry, biotechnology, and the like. It is apparently that in addition to the above description and examples than as specifically described, the present disclosure can also be achieved in other ways. Other aspects within the scope of the disclosure and improvement of the present disclosure will be apparent to the ordinary skilled in the art. According to the teachings of the present disclosure, many modifications and variations are possible, and therefore it is within the scope of the present disclosure.

Unless otherwise indicated herein, the temperature unit "degrees" refers to Celsius degrees, namely ° C.

All references that have been referred to in the present application are incorporated by reference in their entirety for all purposes.

REFERENCES

1. Adzic et al. Behav. Brain Res. 291, 2015.
2. Banasr et al., Biological psychiatry 64, 863-870, 2008.
3. Cotter et al., Archives of general psychiatry 58, 545-553, 2001.
4. Coyle et al., Archives of general psychiatry 57, 90-93, 2000.
5. Cui et al. Nature 554, 323-327.
6. Czeh et al., the journal of the European College of Neuropsychopharmacology 23, 171-185, 2013.
7. Hamilton et al., Frontiers in neuroenergetics 2, 2010.
8. Hiroshi et al., Physiological Reviews 90, 291-366, 2010.
9. Kharade et al., Molecular Pharmacology 94, 926-937, 2018.
10. Ohno et al., Brain Research 1178, 44-51, 2007.
11. Rajkowska et al., CNS & neurological disorders drug targets 6, 219-233, 2007.
12. Schulz et al., Neurobiol Learn Mem 93, 291, 2010.
13. Wang et al., Psychophamacology 183, 490-499, 2006.

The invention claimed is:

1. A pharmaceutical composition for treating depression in a subject, wherein the depression is characterized by abnormal burst firings of neurons in a lateral habenula (LHb) of the subject, the pharmaceutical composition comprising a therapeutically effective amount of a pharmaceutical agent, wherein the pharmaceutical agent comprises a recombinant vector configured to express in astrocytes in the LHb of the subject a short hairpin RNA (shRNA) molecule, wherein the shRNA molecule comprises two complementary sequences, and one of the two complementary sequences has a nucleotide sequence that is identical to the sequence as set forth in SEQ ID NO. 5.

2. The pharmaceutical composition of claim 1, wherein the recombinant vector is a recombinant viral vector capable of preferentially or specifically targeting the astrocytes of the subject.

3. The pharmaceutical composition of claim 2, wherein the recombinant vector is based on an adeno-associated virus (AAV) of 2/5 serotype (AAV2/5).

4. A method for treating depression in a subject, comprising:
administering to the subject the pharmaceutical composition according to claim 1.

5. The method of claim 4, wherein the recombinant vector is a recombinant viral vector, wherein the administering to the subject the pharmaceutical composition comprises:

obtaining virus particles carrying the recombinant viral vector; and administering the virus particles to the subject.

6. The method of claim 5, wherein the administering the virus particles to the subject is through an injection or an inhalation.

7. The method of claim 4, wherein the pharmaceutical agent in the pharmaceutical composition comprises a small molecule agent capable of inhibiting the activity of the astroglial potassium channel in the astrocytes in the lateral habenula of the subject, wherein the administering to the subject a pharmaceutical composition comprises:

administering the pharmaceutical composition in a systemic manner; or administering the pharmaceutical composition locally to the lateral habenula of the subject.

* * * * *

SEQUENCE LISTING

```
<160> NUMBER OF SEQ ID NOS: 20

<210> SEQ ID NO 1
<211> LENGTH: 19
<212> TYPE: DNA
```

<213> ORGANISM: Rat

<400> SEQUENCE: 1
ggacgacctt cattgacat        19

<210> SEQ ID NO 2
<211> LENGTH: 21
<212> TYPE: DNA
<213> ORGANISM: Rat

<400> SEQUENCE: 2
gctacaagct tctgctcttc t        21

<210> SEQ ID NO 3
<211> LENGTH: 21
<212> TYPE: DNA
<213> ORGANISM: Rat

<400> SEQUENCE: 3
gctcttctcg ccaacctta c        21

<210> SEQ ID NO 4
<211> LENGTH: 19
<212> TYPE: DNA
<213> ORGANISM: Rat

<400> SEQUENCE: 4
ccggaacctt ccttgcaaa        19

<210> SEQ ID NO 5
<211> LENGTH: 21
<212> TYPE: DNA
<213> ORGANISM: Rat

<400> SEQUENCE: 5
gcgtaagagt ctcctcattg g        21

<210> SEQ ID NO 6
<211> LENGTH: 19
<212> TYPE: DNA
<213> ORGANISM: Rat

<400> SEQUENCE: 6
gcccttagtg tgcgcatta        19

<210> SEQ ID NO 7
<211> LENGTH: 1140
<212> TYPE: DNA
<213> ORGANISM: Rat

<400> SEQUENCE: 7
atgacatcag ttgccaaggt ctattacagc cagacgacgc agacagagag ccggccccta        60
gtggctccag gaatacgtcg gaggagggtc ctgacaaaag atggccggag caacgtgaga       120
atggagcata ttgctgacaa gcgtttcctc tacctcaagg atctatggac gaccttcatt       180
gacatgcagt ggcgctacaa gcttctgctc ttctcggcaa cctttgcagg cacttggttc       240
ctctttggcg tggtgtggta tctggtcgct gtggcccacg ggacctgtt ggagctggga       300 cctcctgcca accacacgcc ctgtgtggtg caggtgcaca cacttactgg ggccttcctc       360
ttctccctcg aatcccagac caccattggc tatggcttcc gctacatcag cgaggaatgc       420
cctctggcca ttgtgcttct cattgcacag ctcgtgctca ccaccattct ggaaatcttc       480

```
atcaccggaa ccttccttgc aaagattgcc cggccaaaga agagggctga gacgatccgt    540
ttcagccagc atgcggttgt ggcttaccac aacgggaagc tttgcctcat gatccgggtg    600
gccaacatgc gtaagagtct cctcattggg tgccaggtga caggcaaact gcttcaaacc    660
caccagacaa aggagggtga gaatattcgg ctcaaccagg tcaatgtgac tttccaagta    720
gacacagcct ctgatagccc ctttctcatt ctacccctga ctttctacca tgtggtagat    780
gagaccagcc ccttgaaaga tctccccctc cgcagcgggg agggtgactt cgagctcgtg    840
ctgatcctaa gtgggacggt ggagtccacc agcgccacct gtcaagttcg cacttcctat    900
ctaccggagg agatcctctg gggctacgag ttcacacctg ctatctcact gtcagccagt    960
ggcaaatacg tggctgactt cagcctttt gaccaggttg tgaaagtggc gtcccccggt    1020
ggtctccgag atagcaccgt acgttatgga gacccagaaa agctcaagtt ggaggagtca    1080
ttaagagagc aagctgaaaa ggaaggcagt gcccttagtg tgcgcattag taacgtctga    1140
```

<210> SEQ ID NO 8
<211> LENGTH: 379
<212> TYPE: PRT
<213> ORGANISM: Rat

<400> SEQUENCE: 8

```
Met Thr Ser Val Ala Lys Val Tyr Tyr Ser Gln Thr Thr Gln Thr Glu
1               5                   10                  15

Ser Arg Pro Leu Val Ala Pro Gly Ile Arg Arg Arg Arg Val Leu Thr
            20                  25                  30

Lys Asp Gly Arg Ser Asn Val Arg Met Glu His Ile Ala Asp Lys Arg
        35                  40                  45

Phe Leu Tyr Leu Lys Asp Leu Trp Thr Thr Phe Ile Asp Met Gln Trp
    50                  55                  60

Arg Tyr Lys Leu Leu Leu Phe Ser Ala Thr Phe Ala Gly Thr Trp Phe
65                  70                  75                  80

Leu Phe Gly Val Val Trp Tyr Leu Val Ala Val Ala His Gly Asp Leu
                85                  90                  95

Leu Glu Leu Gly Pro Pro Ala Asn His Thr Pro Cys Val Val Gln Val
            100                 105                 110

His Thr Leu Thr Gly Ala Phe Leu Phe Ser Leu Glu Ser Gln Thr Thr
        115                 120                 125

Ile Gly Tyr Gly Phe Arg Tyr Ile Ser Glu Glu Cys Pro Leu Ala Ile
    130                 135                 140

Val Leu Leu Ile Ala Gln Leu Val Leu Thr Thr Ile Leu Glu Ile Phe
145                 150                 155                 160

Ile Thr Gly Thr Phe Leu Ala Lys Ile Ala Arg Pro Lys Lys Arg Ala
                165                 170                 175

Glu Thr Ile Arg Phe Ser Gln His Ala Val Val Ala Tyr His Asn Gly
            180                 185                 190

Lys Leu Cys Leu Met Ile Arg Val Ala Asn Met Arg Lys Ser Leu Leu
        195                 200                 205

Ile Gly Cys Gln Val Thr Gly Lys Leu Leu Gln Thr His Gln Thr Lys
    210                 215                 220

Glu Gly Glu Asn Ile Arg Leu Asn Gln Val Asn Val Thr Phe Gln Val
225                 230                 235                 240

Asp Thr Ala Ser Asp Ser Pro Phe Leu Ile Leu Pro Leu Thr Phe Tyr
                245                 250                 255
```

```
His Val Val Asp Glu Thr Ser Pro Leu Lys Asp Leu Pro Leu Arg Ser
            260                 265                 270

Gly Glu Gly Asp Phe Glu Leu Val Leu Ile Leu Ser Gly Thr Val Glu
        275                 280                 285

Ser Thr Ser Ala Thr Cys Gln Val Arg Thr Ser Tyr Leu Pro Glu Glu
    290                 295                 300

Ile Leu Trp Gly Tyr Glu Phe Thr Pro Ala Ile Ser Leu Ser Ala Ser
305                 310                 315                 320

Gly Lys Tyr Val Ala Asp Phe Ser Leu Phe Asp Gln Val Lys Val
                325                 330                 335

Ala Ser Pro Gly Gly Leu Arg Asp Ser Thr Val Arg Tyr Gly Asp Pro
            340                 345                 350

Glu Lys Leu Lys Leu Glu Glu Ser Leu Arg Glu Gln Ala Glu Lys Glu
        355                 360                 365

Gly Ser Ala Leu Ser Val Arg Ile Ser Asn Val
            370                 375

<210> SEQ ID NO 9
<211> LENGTH: 19
<212> TYPE: DNA
<213> ORGANISM: Artificial Sequence
<220> FEATURE:
<223> OTHER INFORMATION: reverse complementary of Kir mRNA target
      sequence 1

<400> SEQUENCE: 9
atgtcaatga aggtcgtcc                                                19

<210> SEQ ID NO 10
<211> LENGTH: 21
<212> TYPE: DNA
<213> ORGANISM: Artificial Sequence
<220> FEATURE:
<223> OTHER INFORMATION: reverse complementary of Kir mRNA target
      sequence No. 2

<400> SEQUENCE: 10
agaagagcag aagcttgtag c                                             21

<210> SEQ ID NO 11
<211> LENGTH: 21
<212> TYPE: DNA
<213> ORGANISM: Artificial Sequence
<220> FEATURE:
<223> OTHER INFORMATION: reverse complementary of Kir mRNA target
      sequence No. 3

<400> SEQUENCE: 11
gtaaaggttg gcgagaagag c                                             21

<210> SEQ ID NO 12
<211> LENGTH: 19
<212> TYPE: DNA
<213> ORGANISM: Artificial Sequence
<220> FEATURE:
<223> OTHER INFORMATION: reverse complementary of Kir mRNA target
      sequence No. 4

<400> SEQUENCE: 12
tttgcaagga aggttccgg                                                19

<210> SEQ ID NO 13
<211> LENGTH: 21
```

```
<212> TYPE: DNA
<213> ORGANISM: Artificial Sequence
<220> FEATURE:
<223> OTHER INFORMATION: reverse complementary of Kir mRNA target
      sequence No. 5

<400> SEQUENCE: 13
ccaatgagga gactcttacg c                                              21

<210> SEQ ID NO 14
<211> LENGTH: 19
<212> TYPE: DNA
<213> ORGANISM: Artificial Sequence
<220> FEATURE:
<223> OTHER INFORMATION: reverse complementary of Kir mRNA target
      sequence No. 6

<400> SEQUENCE: 14
taatgcgcac actaagggc                                                 19

<210> SEQ ID NO 15
<211> LENGTH: 1140
<212> TYPE: DNA
<213> ORGANISM: Mouse

<400> SEQUENCE: 15
atgacgtcgg tcgctaaggt ctattacagt cagacgactc agacagagag ccgcccccta      60
gtggccccag gaatacgccg gaggagggtc ctcacgaaag acggccggag caatgtgaga     120
atggagcaca ttgctgacaa acgtttcctc tacctcaagg atctatggac gaccttcatt     180
gacatgcaat ggcgctacaa gcttctgctc ttctctgcaa cctttgcagg cacgtggttc     240
ctctttggtg tggtgtggta tctggtagct gtggcccatg ggacctgtt ggagctggga      300 cctcctgcca accacacgcc ttgtgtggtg caggtgcaca cgctcaccgg agccttcctc     360
ttctccctgg aatcccagac caccatcggc tatggcttcc gctacatcag tgaggaatgc     420
ccactggcca tcgtgcttct tattgcgcag ctggtgctca ccaccattct ggaaatcttc     480
atcacaggta ccttccttgc aaagattgcc cggcctaaga gagggccga cgacgatccgc     540 ttcagccagc atgccgttgt ggcttcccat aacgggaagc cttgccttat gatccgggtt     600
gccaatatgc ggaagagtct cctcattgga tgccaggtga caggcaaact gcttcaaacg     660
caccagacaa aggagggtga gaatattcgg ctcaaccagg tcaacgtgac tttccaagta     720
gacacagcct cagacagccc ctttctcatc ctacccctga cttttctacca cgtggtagat     780 gagaccagcc cctaaaaaga tctcccgctc cgcagtgggg aggggggactt tgagctggtg     840 ctgatcctga gtgggacagt ggagtccacc agtgccacct gccaagttcg cacttcctac     900
ctaccggagg agatcctctg gggttacgag ttcacgcctg cgatctcact gtcagccagt     960
ggcaaataca tagctgactt cagccttttc gaccaggttg tgaaagtggc atctcccagt    1020
ggtctccgcg atagcaccgt acgctatgga gaccccgaga agctcaagtt ggaggagtca    1080
ttaagagagc aagctgaaaa ggaaggcagt gcccttagtg tgcgcatcag caacgtctga    1140

<210> SEQ ID NO 16
<211> LENGTH: 379
<212> TYPE: PRT
<213> ORGANISM: Mouse

<400> SEQUENCE: 16

Met Thr Ser Val Ala Lys Val Tyr Tyr Ser Gln Thr Thr Gln Thr Glu
1               5                   10                  15
```

Ser Arg Pro Leu Val Ala Pro Gly Ile Arg Arg Arg Val Leu Thr
            20                  25                  30

Lys Asp Gly Arg Ser Asn Val Arg Met Glu His Ile Ala Asp Lys Arg
        35                  40                  45

Phe Leu Tyr Leu Lys Asp Leu Trp Thr Thr Phe Ile Asp Met Gln Trp
 50                  55                  60

Arg Tyr Lys Leu Leu Leu Phe Ser Ala Thr Phe Ala Gly Thr Trp Phe
65                  70                  75                  80

Leu Phe Gly Val Val Trp Tyr Leu Val Ala Val Ala His Gly Asp Leu
                85                  90                  95

Leu Glu Leu Gly Pro Pro Ala Asn His Thr Pro Cys Val Val Gln Val
            100                 105                 110

His Thr Leu Thr Gly Ala Phe Leu Phe Ser Leu Glu Ser Gln Thr Thr
        115                 120                 125

Ile Gly Tyr Gly Phe Arg Tyr Ile Ser Glu Glu Cys Pro Leu Ala Ile
    130                 135                 140

Val Leu Leu Ile Ala Gln Leu Val Leu Thr Thr Ile Leu Glu Ile Phe
145                 150                 155                 160

Ile Thr Gly Thr Phe Leu Ala Lys Ile Ala Arg Pro Lys Lys Arg Ala
                165                 170                 175

Glu Thr Ile Arg Phe Ser Gln His Ala Val Val Ala Ser His Asn Gly
            180                 185                 190

Lys Pro Cys Leu Met Ile Arg Val Ala Asn Met Arg Lys Ser Leu Leu
        195                 200                 205

Ile Gly Cys Gln Val Thr Gly Lys Leu Leu Gln Thr His Gln Thr Lys
    210                 215                 220

Glu Gly Glu Asn Ile Arg Leu Asn Gln Val Asn Val Thr Phe Gln Val
225                 230                 235                 240

Asp Thr Ala Ser Asp Ser Pro Phe Leu Ile Leu Pro Leu Thr Phe Tyr
                245                 250                 255

His Val Val Asp Glu Thr Ser Pro Leu Lys Asp Leu Pro Leu Arg Ser
            260                 265                 270

Gly Glu Gly Asp Phe Glu Leu Val Leu Ile Leu Ser Gly Thr Val Glu
        275                 280                 285

Ser Thr Ser Ala Thr Cys Gln Val Arg Thr Ser Tyr Leu Pro Glu Glu
    290                 295                 300

Ile Leu Trp Gly Tyr Glu Phe Thr Pro Ala Ile Ser Leu Ser Ala Ser
305                 310                 315                 320

Gly Lys Tyr Ile Ala Asp Phe Ser Leu Phe Asp Gln Val Val Lys Val
                325                 330                 335

Ala Ser Pro Ser Gly Leu Arg Asp Ser Thr Val Arg Tyr Gly Asp Pro
            340                 345                 350

Glu Lys Leu Lys Leu Glu Glu Ser Leu Arg Glu Gln Ala Glu Lys Glu
        355                 360                 365

Gly Ser Ala Leu Ser Val Arg Ile Ser Asn Val
    370                 375

<210> SEQ ID NO 17
<211> LENGTH: 1140
<212> TYPE: DNA
<213> ORGANISM: Homo sapiens

<400> SEQUENCE: 17
atgacgtcag ttgccaaggt gtattacagt cagaccactc agacagaaag ccggccccta        60

-continued

```
atgggcccag ggatacgacg gcggagagtc ctgacaaaag atggtcgcag caacgtgaga     120
atggagcaca ttgccgacaa cgcttcctc tacctcaagg acctgtggac aaccttcatt     180
gacatgcagt ggcgctacaa gcttctgctc ttctctgcga cctttgcagg cacatggttc     240
ctctttggcg tggtgtggta tctggtagct gtggcacatg ggacctgct ggagctggac      300
cccccggcca accacacccc ctgtgtggta caggtgcaca cactcactgg agccttcctc     360
ttctcccttg aatcccaaac caccattggc tatggcttcc gctacatcag tgaggaatgt     420
ccactggcca ttgtgcttct tattgcccag ctggtgctca ccaccatcct ggaaatcttc     480
atcacaggta ccttcctggc gaagattgcc cggcccaaga gcgggctga ccattcgt       540
ttcagccagc atgcagttgt ggcctcccac aatggcaagc cctgcctcat gatccgagtt     600
gccaatatgc gcaaaagcct cctcattggc tgccaggtga caggaaaact gcttcagacc     660
caccaaacca aggaagggga aacatccgg ctcaaccagg tcaatgtgac tttccaagta     720
gacacagcct ctgacagccc cttccttatt ctaccccta ccttctatca tgtggtagat      780
gagaccagtc ccttgaaaga tctccctctt cgcagtggtg agggtgactt tgagctggtg     840
ctgatcctaa gtgggacagt ggagtccacc agtgccacct gtcaggtgcg cacttcctac     900
ctgccagagg agatcctttg gggctacgag ttcacacctg ccatctcact gtcagccagt     960
ggtaaataca tagctgactt tagccttttt gaccaagttg tgaaagtggc ctctcctagt    1020
ggcctccgtg acagcactgt acgctacgga gaccctgaaa agctcaagtt ggaggagtca    1080
ttaagggagc aagctgagaa ggagggcagt gcccttagtg tgcgcatcag caatgtctga    1140
```

```
<210> SEQ ID NO 18
<211> LENGTH: 379
<212> TYPE: PRT
<213> ORGANISM: Homo sapiens

<400> SEQUENCE: 18
```

Met Thr Ser Val Ala Lys Val Tyr Tyr Ser Gln Thr Thr Gln Thr Glu
1               5                   10                  15

Ser Arg Pro Leu Met Gly Pro Gly Ile Arg Arg Arg Val Leu Thr
            20                  25                  30

Lys Asp Gly Arg Ser Asn Val Arg Met Glu His Ile Ala Asp Lys Arg
        35                  40                  45

Phe Leu Tyr Leu Lys Asp Leu Trp Thr Thr Phe Ile Asp Met Gln Trp
    50                  55                  60

Arg Tyr Lys Leu Leu Leu Phe Ser Ala Thr Phe Ala Gly Thr Trp Phe
65                  70                  75                  80

Leu Phe Gly Val Val Trp Tyr Leu Val Ala Val Ala His Gly Asp Leu
                85                  90                  95

Leu Glu Leu Asp Pro Pro Ala Asn His Thr Pro Cys Val Val Gln Val
            100                 105                 110

His Thr Leu Thr Gly Ala Phe Leu Phe Ser Leu Glu Ser Gln Thr Thr
        115                 120                 125

Ile Gly Tyr Gly Phe Arg Tyr Ile Ser Glu Glu Cys Pro Leu Ala Ile
    130                 135                 140

Val Leu Leu Ile Ala Gln Leu Val Leu Thr Thr Ile Leu Glu Ile Phe
145                 150                 155                 160

Ile Thr Gly Thr Phe Leu Ala Lys Ile Ala Arg Pro Lys Lys Arg Ala
                165                 170                 175

Glu Thr Ile Arg Phe Ser Gln His Ala Val Val Ala Ser His Asn Gly

```
                    180                 185                 190
Lys Pro Cys Leu Met Ile Arg Val Ala Asn Met Arg Lys Ser Leu Leu
        195                 200                 205

Ile Gly Cys Gln Val Thr Gly Lys Leu Leu Gln Thr His Gln Thr Lys
    210                 215                 220

Glu Gly Glu Asn Ile Arg Leu Asn Gln Val Asn Val Thr Phe Gln Val
225                 230                 235                 240

Asp Thr Ala Ser Asp Ser Pro Phe Leu Ile Leu Pro Leu Thr Phe Tyr
                245                 250                 255

His Val Val Asp Glu Thr Ser Pro Leu Lys Asp Leu Pro Leu Arg Ser
                260                 265                 270

Gly Glu Gly Asp Phe Glu Leu Val Leu Ile Leu Ser Gly Thr Val Glu
        275                 280                 285

Ser Thr Ser Ala Thr Cys Gln Val Arg Thr Ser Tyr Leu Pro Glu Glu
        290                 295                 300

Ile Leu Trp Gly Tyr Glu Phe Thr Pro Ala Ile Ser Leu Ser Ala Ser
305                 310                 315                 320

Gly Lys Tyr Ile Ala Asp Phe Ser Leu Phe Asp Gln Val Val Lys Val
                325                 330                 335

Ala Ser Pro Ser Gly Leu Arg Asp Ser Thr Val Arg Tyr Gly Asp Pro
                340                 345                 350

Glu Lys Leu Lys Leu Glu Glu Ser Leu Arg Glu Gln Ala Glu Lys Glu
        355                 360                 365

Gly Ser Ala Leu Ser Val Arg Ile Ser Asn Val
        370                 375

<210> SEQ ID NO 19
<211> LENGTH: 20
<212> TYPE: DNA
<213> ORGANISM: Artificial Sequence
<220> FEATURE:
<223> OTHER INFORMATION: synthesized

<400> SEQUENCE: 19
gccggaacct tccttgcaaa                                           20

<210> SEQ ID NO 20
<211> LENGTH: 20
<212> TYPE: DNA
<213> ORGANISM: Artificial Sequence
<220> FEATURE:
<223> OTHER INFORMATION: synthesized

<400> SEQUENCE: 20
tttgcaagga aggttccggc                                           20
```